United States Patent
Weiner et al.

(10) Patent No.: US 8,758,347 B2
(45) Date of Patent: Jun. 24, 2014

(54) DYNAMIC BONE PLATE

(75) Inventors: Lon Weiner, Rumson, NJ (US); Stuart D. Katchis, Scarsdale, NY (US); Arthur A. Alfaro, Colts Neck, NJ (US); Willem H. P. Van Iperen, Westfield, NJ (US)

(73) Assignee: Nextremity Solutions, Inc., Red Bank, NJ (US)

( * ) Notice: Subject to any disclaimer, the term of this patent is extended or adjusted under 35 U.S.C. 154(b) by 241 days.

(21) Appl. No.: 13/051,666

(22) Filed: Mar. 18, 2011

(65) Prior Publication Data
US 2011/0230885 A1 Sep. 22, 2011

Related U.S. Application Data

(60) Provisional application No. 61/322,172, filed on Apr. 8, 2010, provisional application No. 61/315,815, filed on Mar. 19, 2010.

(51) Int. Cl.
*A61B 17/80* (2006.01)
*A61B 17/00* (2006.01)
(52) U.S. Cl.
CPC ... *A61B 17/8009* (2013.01); *A61B 2017/00221* (2013.01); *A61B 17/8019* (2013.01); *A61B 17/8042* (2013.01)
USPC .............................. 606/71; 606/282; 606/290
(58) Field of Classification Search
USPC ................................................ 606/280–299
See application file for complete search history.

(56) References Cited

U.S. PATENT DOCUMENTS

| 3,866,607 A | 2/1975 | Forsythe et al. |
| 3,900,025 A * | 8/1975 | Barnes, Jr. .................... 606/71 |
| 5,129,903 A | 7/1992 | Luhr et al. |

(Continued)

FOREIGN PATENT DOCUMENTS

| FR | 2690068 | 2/1992 |
| FR | 2892617 | 5/2007 |

(Continued)

OTHER PUBLICATIONS

Zdeblick et al., Anterior spinal fixation after lumbar corpectomy. A study in dogs., The Journal of Bone and Joint Surgery. American Volume, 1991, vol. 73, issue 4:527-34.

(Continued)

*Primary Examiner* — Michael T Schaper
*Assistant Examiner* — Tracy Kamikawa
(74) *Attorney, Agent, or Firm* — Heslin Rothenberg Farley & Mesiti P.C.

(57) ABSTRACT

A plate for adjusting the position of a first piece of bone with respect to a second piece of bone, comprising a first section comprising a first upper exterior surface, a first lower exterior surface, a first outer edge, a first distal end, a first coupling end across the first section from the first distal end, at least one first section bone screw hole, and a first bone screw in the at least one first section bone screw hole, a second section comprising a second upper exterior surface, a second lower exterior surface, a second outer edge, a second distal end, a second coupling end across the second section from the second distal end, at least one second section bone screw hole, and a second bone screw in the at least one second section bone screw hole, and a gear disposed between the first section and the second section.

12 Claims, 20 Drawing Sheets

(56) References Cited

U.S. PATENT DOCUMENTS

| | | | |
|---|---|---|---|
| 5,630,816 | A | 5/1997 | Kambin |
| 5,702,395 | A | 12/1997 | Hopf |
| 5,713,900 | A | 2/1998 | Benzel et al. |
| 5,928,231 | A | 7/1999 | Klein et al. |
| 5,947,966 | A | 9/1999 | Drewry et al. |
| 5,993,449 | A | 11/1999 | Schlapfer et al. |
| 6,106,527 | A | 8/2000 | Wu et al. |
| 6,113,599 | A | 9/2000 | Landsberger |
| 6,126,660 | A | 10/2000 | Dietz |
| 6,261,291 | B1 * | 7/2001 | Talaber et al. ............ 606/281 |
| 6,264,658 | B1 | 7/2001 | Lee et al. |
| 6,533,787 | B1 | 3/2003 | Lenke et al. |
| 6,540,769 | B1 | 4/2003 | Miller, III |
| 6,565,569 | B1 | 5/2003 | Assaker et al. |
| 6,807,772 | B2 * | 10/2004 | Halter ....................... 49/39 |
| 6,852,113 | B2 | 2/2005 | Nathanson et al. |
| 6,940,209 | B2 | 9/2005 | Henderson |
| 6,964,664 | B2 | 11/2005 | Fried et al. |
| 7,029,472 | B1 | 4/2006 | Fortin |
| 7,214,226 | B2 | 5/2007 | Alleyne |
| 7,611,526 | B2 | 11/2009 | Carl et al. |
| 7,635,364 | B2 | 12/2009 | Barrall et al. |
| 2003/0050641 | A1 | 3/2003 | Mommaerts |
| 2004/0030395 | A1 | 2/2004 | Blunn et al. |
| 2004/0097938 | A1 | 5/2004 | Alleyne |
| 2004/0127900 | A1 | 7/2004 | Konieczynski et al. |
| 2004/0162558 | A1 | 8/2004 | Hegde et al. |
| 2004/0236329 | A1 | 11/2004 | Panjabi |
| 2005/0043732 | A1 | 2/2005 | Dalton |
| 2006/0036240 | A1 | 2/2006 | Colleran et al. |
| 2006/0195087 | A1 | 8/2006 | Sacher et al. |
| 2007/0123879 | A1 * | 5/2007 | Songer et al. ............ 606/69 |
| 2007/0123880 | A1 | 5/2007 | Medoff |
| 2007/0123881 | A1 * | 5/2007 | Ralph et al. ............ 606/69 |
| 2007/0270855 | A1 | 11/2007 | Partin |
| 2007/0293863 | A1 | 12/2007 | Reimels et al. |
| 2008/0114359 | A1 * | 5/2008 | Murner et al. ............ 606/66 |
| 2008/0147124 | A1 | 6/2008 | Haidukewych et al. |
| 2009/0157121 | A1 | 6/2009 | Harris et al. |
| 2009/0192514 | A1 | 7/2009 | Feinberg et al. |
| 2009/0234359 | A1 | 9/2009 | Onoue et al. |

FOREIGN PATENT DOCUMENTS

| | | |
|---|---|---|
| FR | 2900563 | 11/2007 |
| GB | 1499566 | 2/1978 |
| WO | WO 87/01026 | 2/1987 |
| WO | WO 98/08454 | 3/1998 |
| WO | WO 01/12087 | 2/2001 |
| WO | WO 2005/079684 | 9/2005 |
| WO | WO 2007/011213 | 1/2007 |
| WO | WO 2007/042638 | 4/2007 |
| WO | WO 2007/126622 | 11/2007 |
| WO | WO 2009/062522 | 5/2009 |

OTHER PUBLICATIONS

Instrumentation Systems for Scoliosis Surgery National Scoliosis Foundation Source: http://www.scoliosis.org/resources/medicalupdates/instrumentationsystems.php Date Accessed: Jan. 10, 2008.

Rauzzino, et al., Surgical approaches for the management of idiopathic thoracic scoliosis and the indications for combined anterior-posterior technique, Neurosurg Focus, 1999, article 6, issue 5.

Payer and Sottas, Mini-open anterior approach for corpectomy in the thoracolumbar spine, Dec. 3, 2007, Surgical Neurology, 2008, vol. 69, issue 1, pp. 25-31.

Wua et al., Animal model for evaluation of strain gauge in mandibular distraction osteogenesis in rabbits, British Journal of Oral and Maxillofacial Surgery, 2007, vol. 45, issue 8, pp. 633-636.

Millera and Goswamia, A review of locking compression plate biomechanics and their advantages as internal fixators in fracture healing, Clinical Biomechanics, 2007, vol. 22, issue 10, pp. 1049-1062.

FR2900563 published Nov. 9, 2007, abstract only in English, downloaded from espacenet.com, 1 page.

FR2892617 published May 4, 2007, abstract only in English, downloaded from espacenet.com, 2 pages.

FR2690068 published Oct. 22, 1993, abstract only in English, downloaded from espacenet.com, 2 pages.

International Search Report dated May 20, 2011 in related PCT Application No. PCT/US11/29119 filed Mar. 19, 2011.

* cited by examiner

DYNAMIC BONE PLATE

CROSS-REFERENCE TO RELATED APPLICATIONS

The present application claims the benefit of U.S. Provisional Application Ser. No. 61/322,172 filed 8 Apr. 2010; and U.S. Provisional Application Ser. No. 61/315,815 filed 19 Mar. 2010; which are incorporated herein by reference in their entireties.

BACKGROUND

The present application relates to plates for aligning bone pieces.

Numerous devices that join or distract bone pieces have been described. See, e.g., U.S. Pat. No. 3,866,607; U.S. Patent Application Publications 2005/0043732, 2006/0036240, 2007/0123880, 2007/0270855, 2007/0293863, 2008/0147124, 2009/0234359, and 2009/0192514; and PCT Patent Publications WO 2007/126622 and WO 2009/062522. However, to the applicants' knowledge, no such device provides for both compression and distraction of the bone pieces, with precise fine adjustment of the degree of compression or distraction. A device providing that variety of functions is useful for an array of treatments including fracture repair, bone fusion and distraction osteogenesis. The present invention provides such a device.

SUMMARY

Provided is a plate for aligning bone pieces through compression or distraction of the pieces of bone, including separated pieces of bone. More specifically, a plate is provided that joins bone pieces and that includes a mechanism that allows for precise alignment of the bone pieces. The plate comprises a first section comprising a first upper exterior surface, a first lower exterior surface, a first outer edge, a first distal end, a first coupling end across the first section from the first distal end, at least one first section bone screw hole, and a first bone screw in the at least one first section bone screw hole; a second section comprising a second upper exterior surface, a second lower exterior surface, a second outer edge, a second distal end, a second coupling end across the second section from the second distal end, at least one second section bone screw hole, and a second bone screw in the at least one second section bone screw hole; a gear disposed between the first section and the second section, the gear comprising a rotating unit; a first section gear strip engaging the gear and joined to the first section; and a second section gear strip engaging the gear and joined to the second section. Rotating the rotating unit of the plate in a first direction rotates the gear on the first section gear strip and the second section gear strip, to move the first section toward the second section, and rotating the rotating unit in a second direction rotates the gear on the first section gear strip and the second section gear strip to move the first section away from the second section.

Also provided is a method of adjusting the position of a first bone piece with respect to a second bone piece. The method comprises applying the above-described plate to the first bone piece and second bone piece by placing the first section on the first bone piece and the second section on the second bone piece; screwing the bone screw(s) of the first section into the first bone piece and screwing the bone screw(s) of the second section into the second bone piece; and rotating the rotating unit until the first bone piece is in the desired position with respect to the second bone piece.

Additionally, a locking ring suitable for preventing a bone screw having a head and spiraling threads from backing out of a bone plate is provided. The locking ring comprises an interior edge and an exterior edge; a plurality of radial slots partially cut through the locking ring from the interior edge toward the exterior edge; and an expansion unit of the locking ring diameter. In these embodiments, the locking ring is narrower than the head of the bone screw and wider than the threads of the bone screw.

Further, another locking ring suitable for preventing a bone screw having a head and spiraling threads from backing out of a bone plate is provided. The ring comprises an interior edge and an exterior edge; a plurality of radial slots partially cut through the locking ring from the interior edge toward the exterior edge; a expansion unit of the locking ring diameter, and a contraction unit of the locking ring diameter. In these embodiments, the locking ring is narrower than the head of the bone screw and wider than the threads of the bone screw.

Additionally provided is a method of preventing a bone screw from backing out of a bone plate using the above-identified locking rings. Here, the bone plate comprises the bone screw, a screw hole an outer edge and a ring slot. The ring slot circumscribes the bone screw hole and extends to the outer edge of the plate; each ring slot comprises a ring slot upper surface and a ring slot lower surface. Also, the bone screw hole passes through the ring slot upper surface and the ring slot lower surface. In these embodiments, the bone screw has a head wider than the interior edge of the locking ring, a spiraling thread, and a flat outer face and tapered inner face. Further, the bone screw hole has a diameter wider than the screw head at the upper surface of the plate and the ring slot upper surface but narrower than the locking ring, and a diameter narrower than the screw head at the ring slot lower surface. The method comprises placing the locking ring through the ring slot to the bone screw hole; placing the bone screw hole over a bone; putting the bone screw into the bone screw hole; and screwing the bone screw into the bone such that the tapered inner face of the head of the screw encounters the locking ring and expands the locking ring radially outward until the head of the bone screw passes the interior edge of the locking ring, allowing the locking ring to resume its original shape, extending over the flat outer face of the bone screw.

Also, another method of preventing a bone screw from backing out of a bone plate is provided using the above identified locking rings having a expansion unit of the locking ring diameter and a contraction unit of the locking ring diameter. Here, the bone plate comprises the bone screw, a screw hole an outer edge and a ring seat. In these embodiments, the bone screw hole comprises a ring seat disposed below the upper exterior surface of the plate, the ring seat circumscribing the bone screw hole, the ring seat allowing placement of a locking ring by contracting the diameter of the locking ring and placing the locking ring into the ring seat; and the ring seat comprises a ring seat upper surface and a ring seat lower surface, the bone screw hole passing through the ring seat upper surface and the ring seat lower surface. Further, the bone screw hole has a diameter wider than the screw head, but narrower than the locking ring, at the upper surface of the plate and the first ring seat upper surface, and a diameter narrower than the screw head at the ring seat lower surface. The method comprises contracting the diameter of the locking ring and placing the locking ring into the ring seat; placing the bone screw hole over a bone; putting the bone screw into the bone screw hole; and screwing the bone screw into the bone such that the tapered inner face of the head of the screw encounters the locking ring and expands the locking ring radially outward until the head of the bone screw passes the interior edge of the locking ring, allowing the locking ring to resume its original shape, extending over the flat outer face of the bone screw.

DETAILED DESCRIPTION

As used herein, the singular forms "a", "an" and "the" are intended to include the plural forms as well, unless the context clearly indicates otherwise. Additionally, the use of "or" is intended to include "and/or", unless the context clearly indicates otherwise.

Figure 4A:
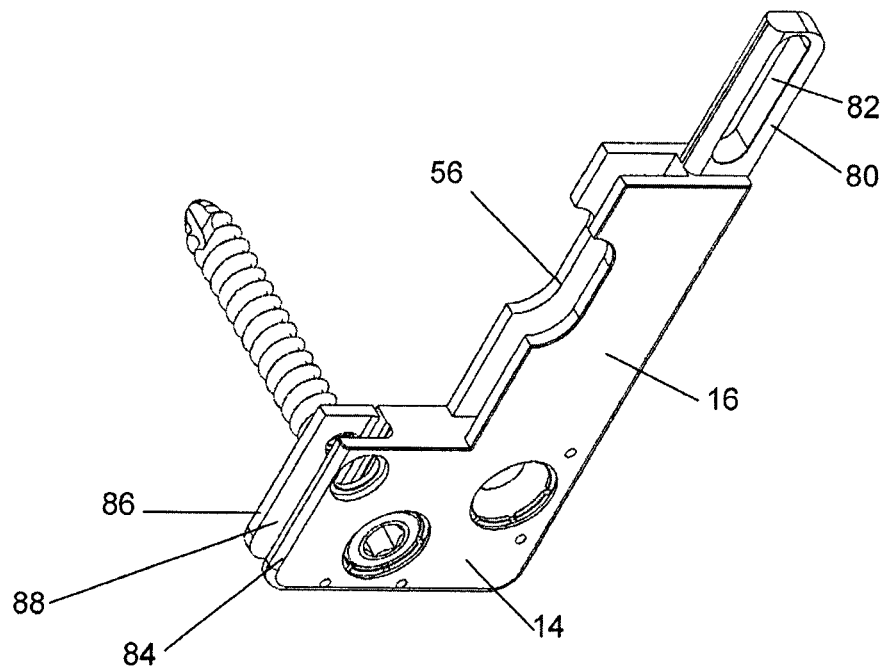
FIG. 4 is a front perspective view (Panel A) and a back perspective view (Panel B) of a section of a bone plate in accordance with an illustrative embodiment.
Figure 4B:
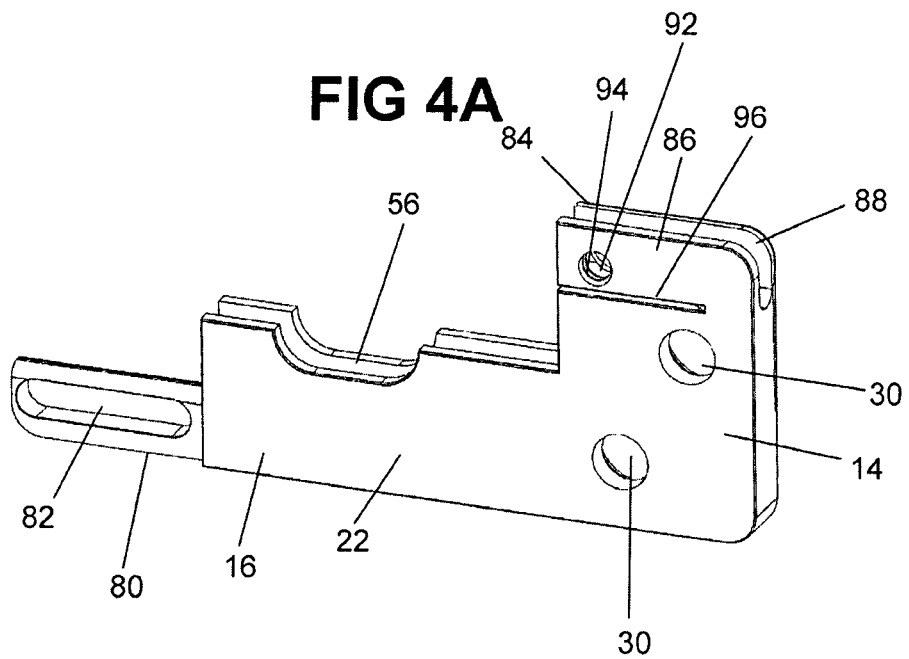
Figure 5:
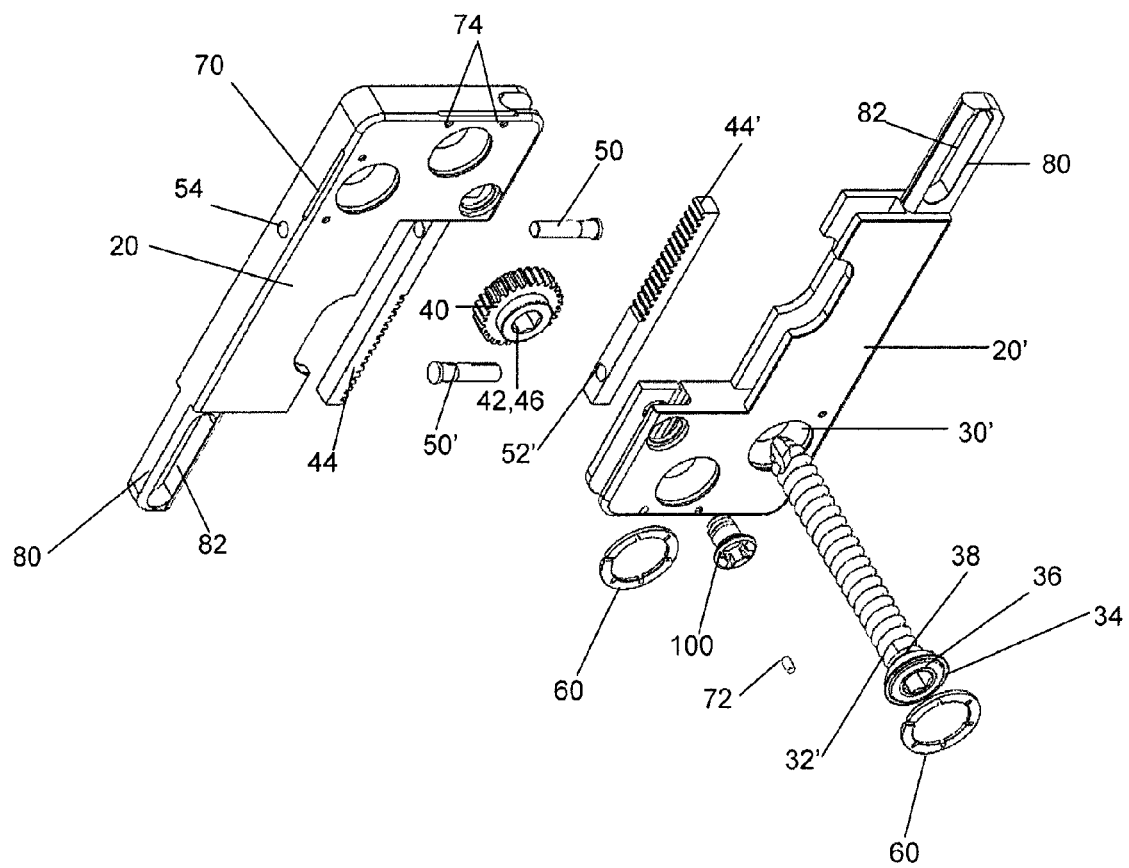
FIG. 5 is an exploded view of a bone plate in accordance with an illustrative embodiment.

Provided herein is a plate for compressing or distracting pieces of bone. The plate provides tight control of the degree of compression or distraction applied to the bone pieces. In the embodiments illustrated in the figures provided herein, the plate comprises two identical interlocking sections. In some embodiments, the plate 10 comprises a first section 12 comprising a first upper exterior surface 20, a first lower exterior surface 22 (FIG. 4B), a first outer edge 24, a first distal end 26, a first coupling end 28 across the first section 12 from the first distal end 26, at least one first section bone screw hole 30, and a first bone screw 32 in the at least one first section bone screw hole 30. In various embodiments, the plate 10 also comprises a second section 12' comprising a second upper exterior surface 20', a second lower exterior surface, a second outer edge 24', a second distal end 26', a second coupling end 28' across the second section 12' from the second distal end 26', at least one second section bone screw hole 30', and a second bone screw 32' in the at least one second section bone screw hole 30'.

Figure 2:
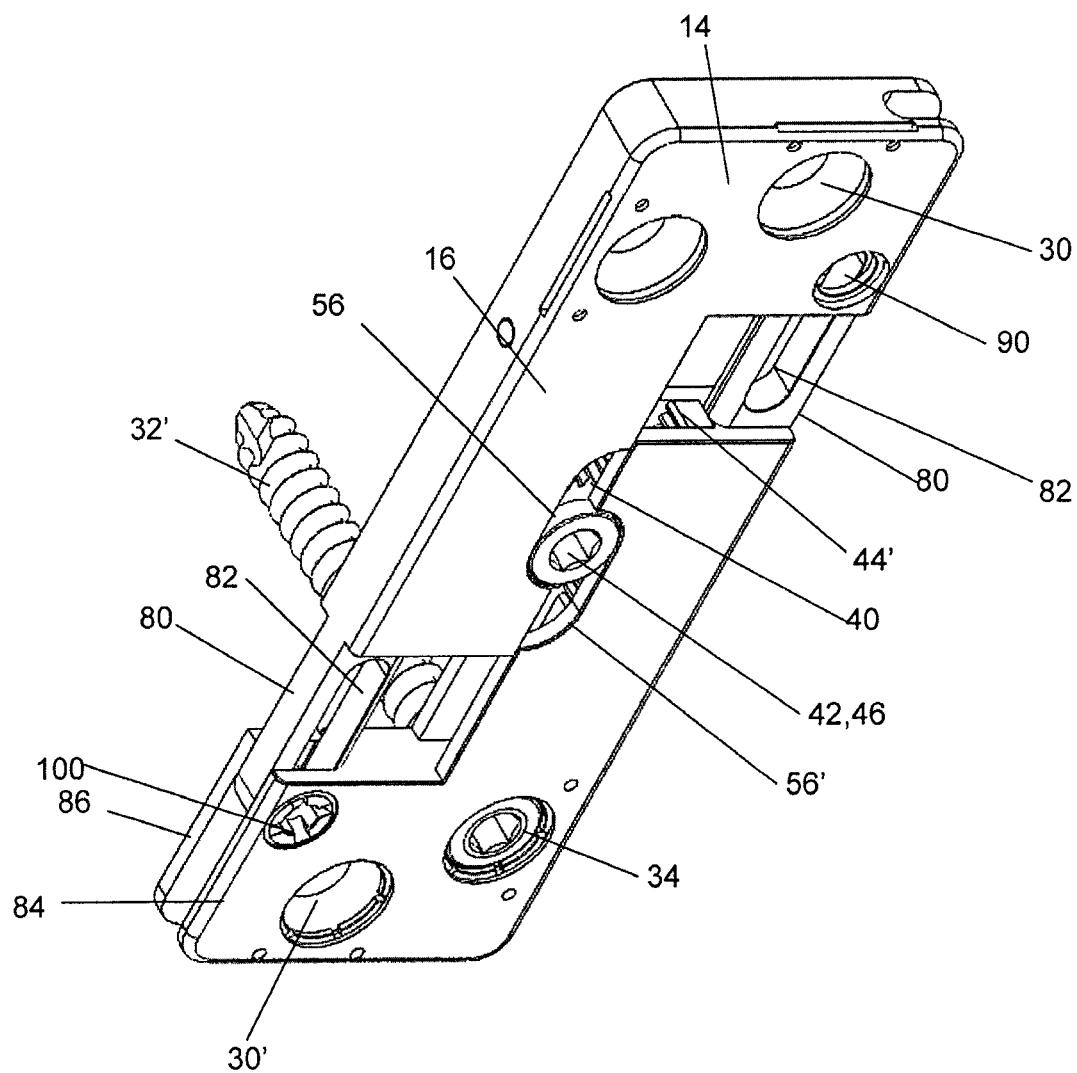
FIG. 2 is a perspective view of the front of a bone plate in the fully open position in accordance with an illustrative embodiment.

The plate 10 also comprises a gear 40 disposed between the first section 12 and the second section 12'. In some embodiments, the gear is disposed in U-shaped recesses 56, 56' in the first section 12 and the second section 12', respectively (FIG. 2). The gear 40 comprises a rotating unit 42. A first section gear strip 44 is also provided. The first section gear strip 44 engages the gear 40 and is joined to the first section 12. A second section gear strip 44' is additionally provided. The second section gear strip 44' engages the gear 40 and is joined to the second section 12'.

Compression is applied to the two bone pieces by rotating the rotating unit 42 in a first direction (counterclockwise in the illustrated embodiments), which rotates the gear 40 on the first section gear strip 44 and the second section gear strip 44', to move the first section 12 toward the second section 12'. Conversely, distraction is applied to the two bone pieces by rotating the rotating unit 42 in a second direction (clockwise in the illustrated embodiments), which rotates the gear 40 on the first section gear strip 44 and the second section gear strip 44' to move the first section 12 away from the second section 12'. In various embodiments, the second direction is opposite the first direction.

The rotating unit can be any known in the art, including ratchets or knobs turned by hand or with a tool. In some embodiments, the rotating unit is a cavity in the gear 40 or a protrusion extending from the gear 40. The cavity or protrusion can have any shape to accommodate any tool, e.g., a screwdriver or wrench, having a complementary shape. In some embodiments, the cavity or protrusion is hexagonal, as in the illustrated embodiment, showing a cavity 46. The tool can be a tool such as a torque wrench or a similar tool having an adjustable setting to limit the amount of force applied by the tool.

In various embodiments, the rotating unit is a motor. The motor can be any micro motor known in the art, for example a piezoelectric motor, e.g., as described in U.S. Pat. No. 6,940,209. Motorized rotating unit are particularly useful when the compression or distraction is varied over time, for example when the compression is increased or decreased over several days or weeks, or if the device is used for distraction osteogenesis, i.e., the lengthening of a bone by the slow distraction of the cut bone such that new bone grows between the cut. Such a procedure often takes weeks or months to achieve sufficient growth. By using a motor to slowly (e.g., 1 mm per day) distract the plate applied between two bone pieces, the plate described herein can be used to practice distraction osteogenesis. In some embodiments, the motor is radio controlled, allowing implantation of the device without having a motor control mechanism extending through the skin. The motor may also include the capability of adjusting the amount of torque applied by the motor.

The motor of these embodiments can further comprise a control means to limit the motor to a set maximum applied force, such that compression applied can be optimized.

In various embodiments, such as the illustrated embodiments, each section of the plate comprises a wide portion 14 toward the distal end and a narrow portion 16 toward the coupling end, where the wide portion 14 is substantially rectangular and the narrow portion 16 is substantially rectangular, elongate and narrower than the wide portion. The bone screws 32, 32' can be disposed in the wide portion 14 and/or the narrow portion 16. In the illustrated embodiments, the at least one bone screw 32, 32' is disposed in the wide portion 14.

Figure 3:
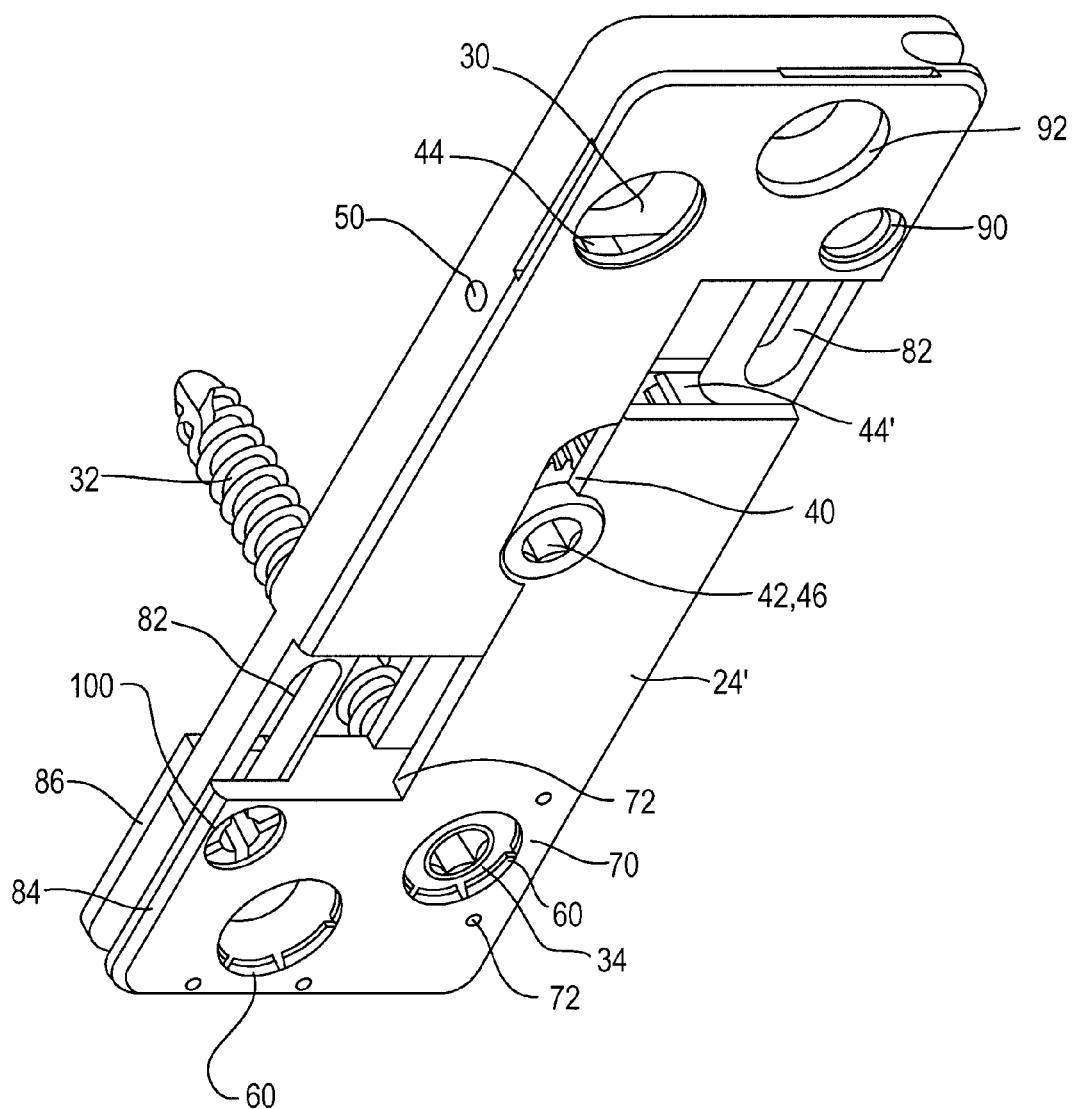
FIG. 3 is a cutaway view of the front a bone plate in the fully open position in accordance with an illustrative embodiment.
Figure 9:
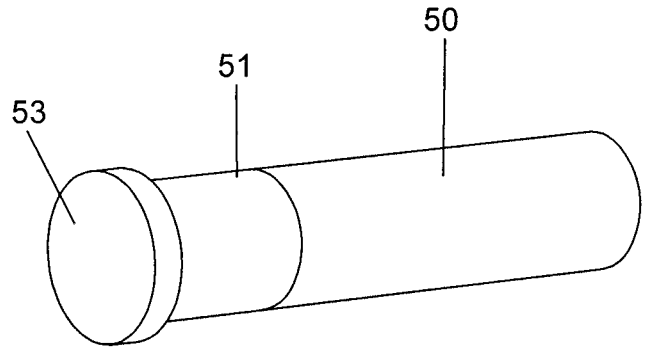
FIG. 9 is a perspective view of a gear strip pin in accordance with an illustrative embodiment.

In some embodiments, the first section gear strip 44 is integral with the first section 12 and the second section gear strip 44' is integral with the second section 12'. In other embodiments, the first section gear strip 44 is joined to the first section 12 by a first gear strip joining means, and the second section gear strip 44' is joined to the second section 12' by a second gear strip joining means. The joining means can be any known in the art, for example a screw, a clip, an adhesive, or a weld. In some embodiments, the first gear strip joining means is a first gear strip pin 50 that passes through a first gear strip hole 52 into a first section gear strip hole 54 and the second gear strip joining means is a second gear strip pin 50' that passes through a second gear strip hole 52' into a second section gear strip hole 54'. This mechanism is best illustrated in FIG. 3. As illustrated, the gear strip pin 50 (see, e.g., FIG. 9) has an indentation 51 and a head 53 such that, when in use, the indentation 51 resides in the gear strip hole 52, where the head 53 prevents passage of the entire gear strip pin 50 into the gear strip hole 52. However, the gear strip pin 50 is not narrowly limited to such embodiments, and can have any shape suitable for joining the gear strip 44, 44' to the section 12, 12'.

The plate can comprise any number of bone screw holes 30, for example 2, 4 or 6. In some embodiments, the first section 12 comprises two first section bone screw holes 30 and two bone screws 32 and the second section 12' comprises two second section bone screw holes 30' and two bone screws 32'. The bone screws may be configured in any configuration. In some embodiments, each bone screw 32 is countersunk in its bone screw hole 30. The plate may also comprise any means to prevent the bone screw 32 from backing out. In some embodiments, each bone screw hole 30 further comprises a locking ring 60 that prevents the bone screw 32 from backing out. As illustrated, the bone screws 32, 32' are 3.5 mm in diameter and 30 mm in length, however, the screw holes can be modified to accommodate any diameter bone screw and the plates can accommodate any length bone screw.

In various embodiments, each bone screw hole comprises a ring slot 70 disposed below the upper exterior surface 20, 20' of the section 12, 12', the ring slot 70 circumscribing the bone screw hole 30 and extending to the outer edge 24, 24' of the section. In these embodiments, the ring slot 70 allows placement of the locking ring 60 through the ring slot 70 to the bone screw hole 30, accommodating and allowing expansion of the locking ring 70 therein.

Figure 7A:
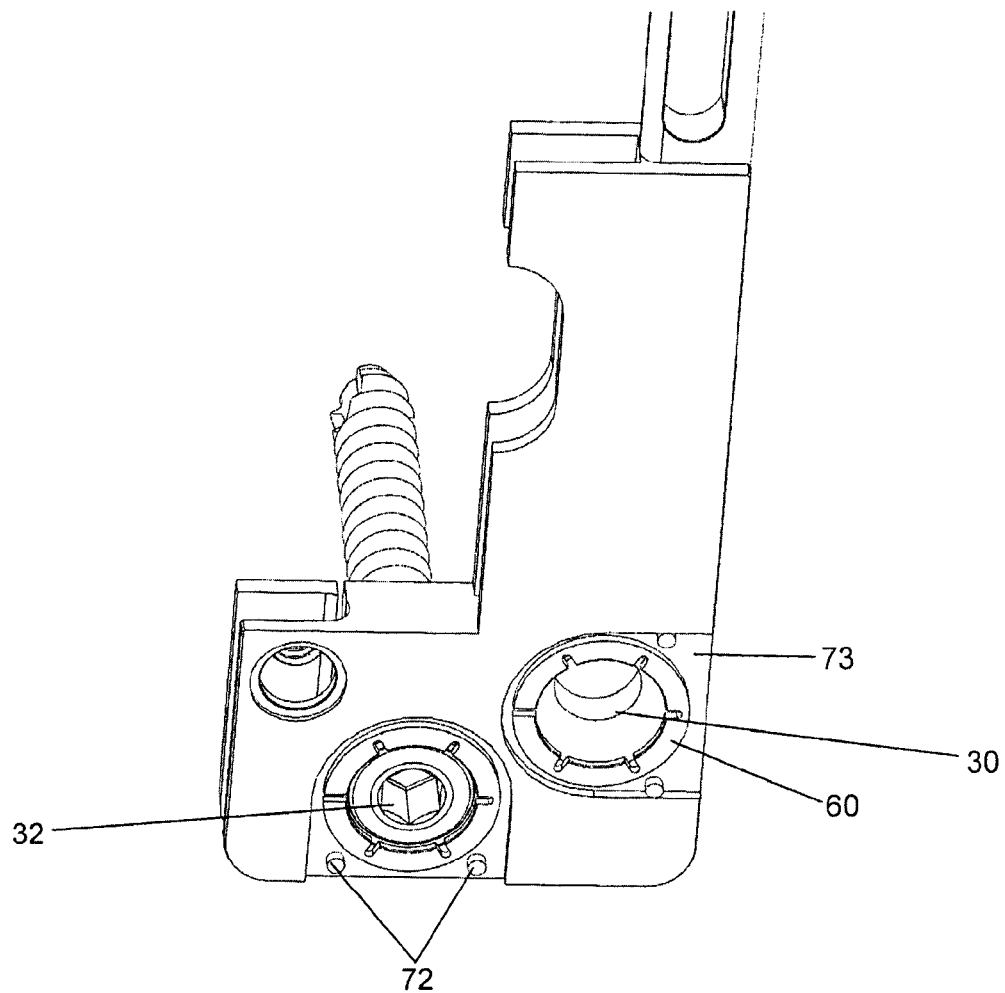
FIG. 7 is a front perspective view of a portion of a section (A) and a perspective view of a locking ring (B) in accordance with an illustrative embodiment.
Figure 7B:
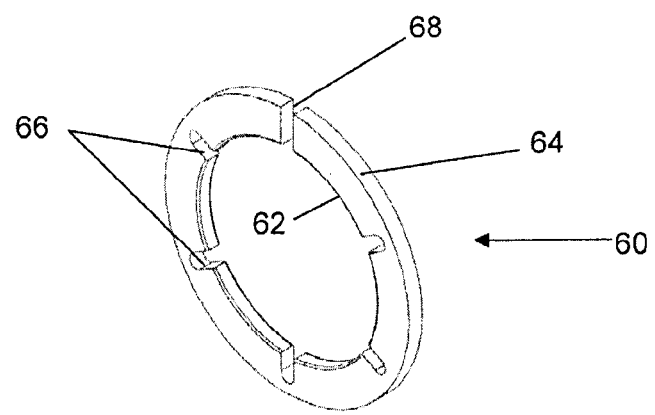
Figure 8A:
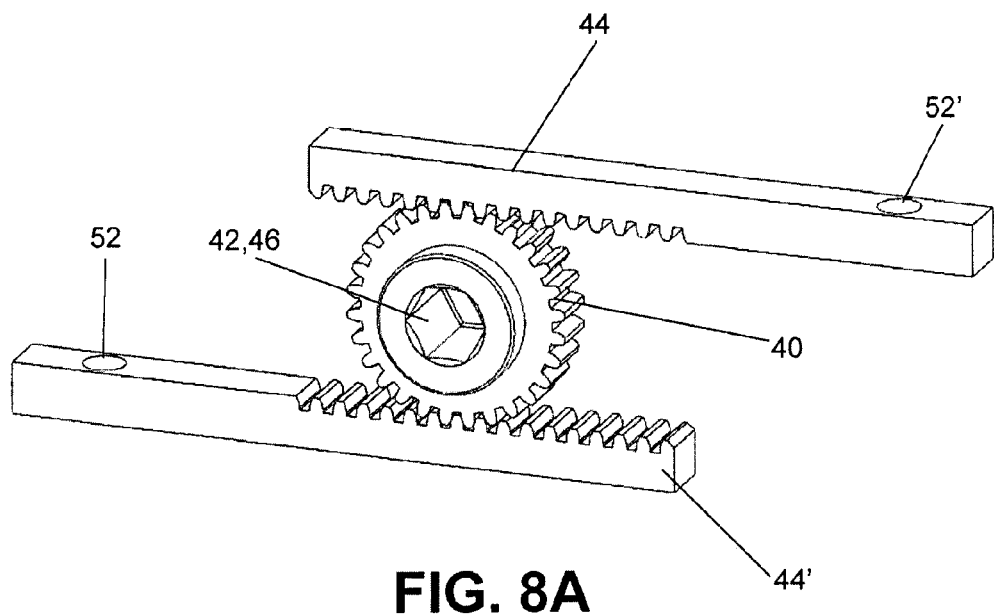
FIG. 8 is perspective views of a gear and gear strips (A) and a gear (B) in accordance with an illustrative embodiment.
Figure 8B:
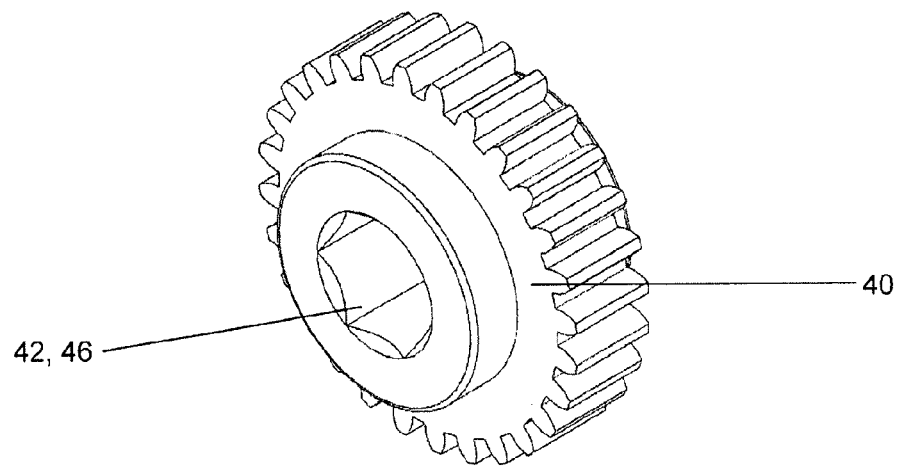

The locking ring 60 can be configured in any configuration known in the art. In some embodiments (See, e.g., FIG. 7B), each locking ring 60 comprises an interior edge 62 and an exterior edge 64; a plurality of radial slots 66 partially cut through the ring 60 from the interior edge 62 toward the exterior edge 64; and a means for allowing expansion of the locking ring diameter. In these embodiments, each bone screw 32 comprises a head 34 wider than the interior edge 62 of the locking ring 60 and having a flat outer face 36 and tapered inner face 38. As such, when the bone screw 32 is screwed into the bone, the tapered inner face 38 of the head 34 of the screw 32 encounters the locking ring 60 and spreads the locking ring 60 radially outward until the head 34 of the bone screw 32 passes the locking ring 60, allowing the locking ring 60 to resume its original shape and preventing the bone screw 32 from backing out.

The locking ring 60 can comprise any means for allowing expansion of the locking ring diameter. Examples include making at least a part of the locking ring from an elastic material or an elastic type material. In the embodiment illustrated in FIG. 7B, the means for allowing expansion of the locking ring is a radial cut 68 through the ring 60 from the interior edge 62 through the exterior edge 64.

Figure 6:
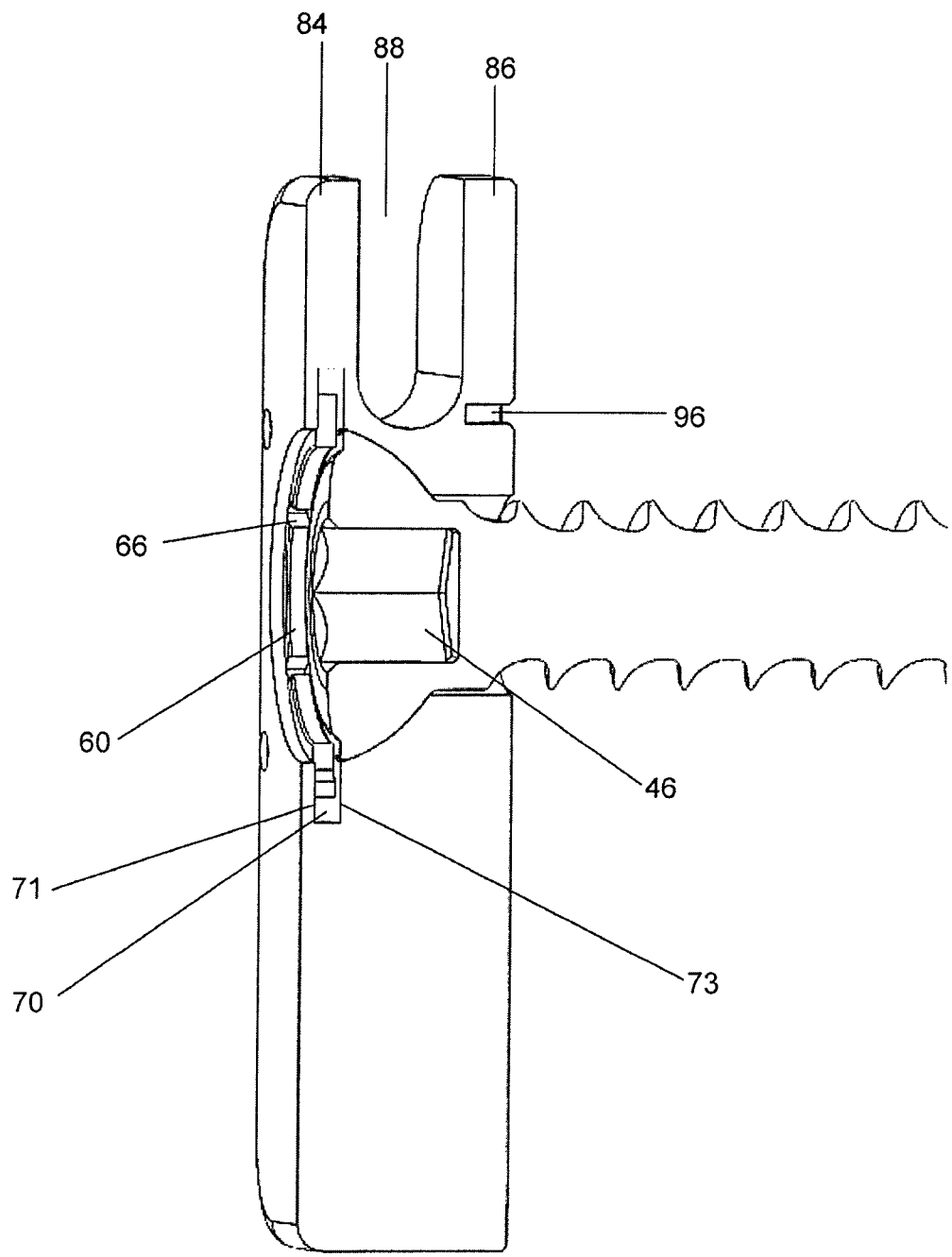
FIG. 6 is a cross-sectional view of a portion of a bone plate in accordance with an illustrative embodiment.

In some embodiments, each ring slot 70 comprises a ring slot upper surface 71 and a ring slot lower surface 73 (FIG. 6), with the bone screw hole 30 passing through the ring slot upper surface 71 and the ring slot lower surface 73. To prevent the bone screw 32 from passing through the bone screw hole 30 at the upper surface, the bone screw hole 30 has a diameter wider than the bone screw head at the upper surface of the section and the ring slot upper surface 71, and a diameter narrower than the screw head at the ring slot lower surface 73.

In these embodiments, the locking ring 60 can be prevented from sliding out of the outer edge of the ring slot by any means, for example at least one (here, two) slot pins 72 disposed through slot pin holes 74 extending from the upper exterior of the section 12, 12' adjacent to the bone screw hole 30, 30'.

In some embodiments (e.g., as illustrated in FIGS. 12-17 and 19), each locking ring 60' further comprises a means for allowing contraction of the locking ring diameter. In these embodiments, each bone screw hole also comprises a ring seat 75 disposed below the upper exterior surface 20, 20' of the section, the ring seat 75 circumscribing the bone screw hole 30, 30', each ring seat 75 allowing placement of a locking ring 60' by contracting the diameter of the locking ring 60' and placing the locking ring 60' into the ring seat 75. In these embodiments, any means known in the art for allowing contraction of the locking ring diameter can be utilized, including making at least a portion of the locking ring with an elastic material or an elastic type material. In the illustrated embodiments, the means for allowing contraction of the locking ring diameter is the removal of a radial section 69 of the locking ring 60', thus leaving a space into which the locking ring can be contracted. See, e.g., FIG. 19.

In some embodiments, each ring seat 75 comprises a ring seat upper surface 77 and a ring seat lower surface 79 (FIG. 17C), where the bone screw hole 30 passes through the ring seat upper surface 77 and the ring seat lower surface 79. Here, the bone screw hole 30 has a diameter wider than the screw head 34, but narrower than the locking ring 60', at the upper surface of the section 20, 20' and the ring seat upper surface 77 and a diameter narrower than the screw head 34 at the ring seat lower surface 79.

The plate can further comprise any mechanism to fix the two sections at any position relative to each other (e.g., at a particular amount of compression). For example, in the embodiment illustrated in FIGS. 1-5, each section 12, 12' further comprises an extension 80 disposed outward from the coupling end 28, 28' of the section 12, 12', wherein the extension 80 is elongate and thinner than the section 12, 12' and wherein the extension 80 further comprises an extension slot 82 circumscribed by, and passing through, the extension 80. In conjunction with the extension 80, the plate further comprises an upper flange 84 disposed at the upper exterior surface 20, 20' outward from the distal end 26, 26' of the section 12, 12' and a lower flange 86 disposed at the lower exterior surface 22, 22' outward from the distal end 26, 26' of the section 12, 12', the upper flange 84 and the lower flange 86 forming a space 88 between them that accommodates an extension 80. In these embodiments, the upper flange 84 comprises an upper flange hole 90 and the lower flange 86 comprises a lower flange hole 92, the upper flange hole 90 aligned with the lower flange hole 92.

Figure 10:
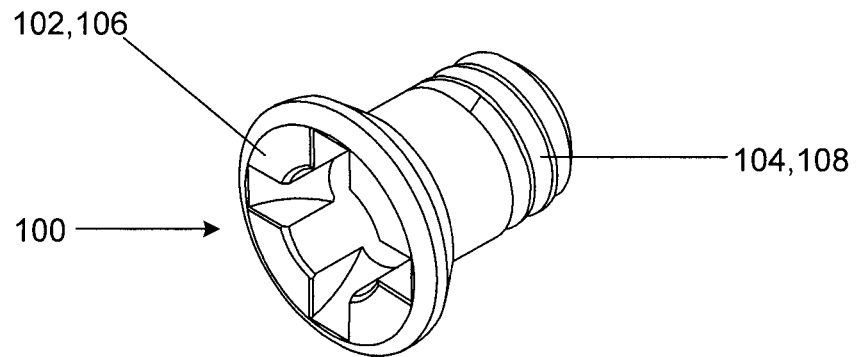
FIG. 10 is a perspective view of a guide screw in accordance with an illustrative embodiment.
Figure 11:
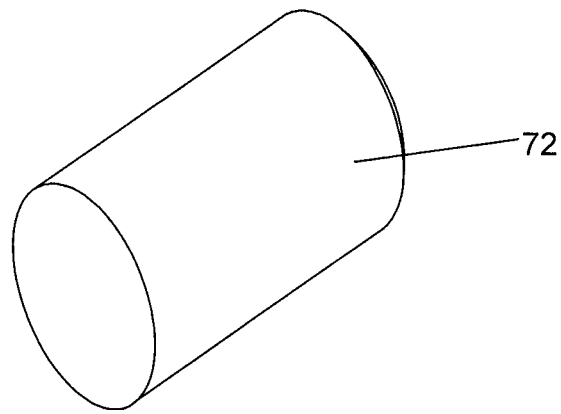
FIG. 11 is a perspective view of a slot pin in accordance with an illustrative embodiment.

In addition, in various embodiments, the lower flange 86 is movable in the direction of the upper flange 84. This movable feature of the lower flange 86 can be effected by any means known in the art, for example by having the area where the lower flange 86 meets the section thinner than the rest of the flange, by deploying a hinge in that area, or by partly separating the lower flange 86 from the lower exterior surface of the distal end of the section, shown in the figures as the separation 96, extending from a corner of the lower flange 86 to beyond an area alongside the lower flange hole 92. In these embodiments, the plate also comprises a guide screw 100 having an upper end 102 and a lower end 104, with a head 106 at the upper end and screw threads 108 at the lower end, the head 106 wider than the flange hole 90 in the upper flange 84 (See, e.g., FIG. 10).

In various embodiments, the guide screw 100 abuts the upper flange hole 90 such that the head of the guide screw 100 is completely below the upper surface of the corresponding section. In those embodiments, the upper flange hole 92 is wider than the head of the guide screw 100 at the upper surface of the corresponding section and is tapered to be narrower than the head of the guide screw 100 below the upper surface.

In some embodiments, the lower flange hole 92 further comprises a helical groove 94 (FIG. 4B) disposed therein to accommodate threads of a screw. In these embodiments, the guide screw 100 is disposed in the flange holes 90, 92 such that the head 106 of the guide screw 100 abuts the upper flange hole 90 with the guide screw 100 extending therethrough to the lower flange hole 92 such that the screw threads 108 at the lower end 104 engage the helical groove 94 disposed in the lower flange hole 92. In those embodiments, screwing the guide screw tightly in the flanges 84, 86 bends the lower flange 86 at the partial separation 96 toward the upper flange 84. Further, the extension 80 of the first section 12 is disposed in the space 88 between the upper flange 84 and the lower flange 86 of the second section 12' and the extension 80 of the second section 12' is disposed in the space 88 between the upper flange 84 and the lower flange 86 of the first section 12 and screwing the guide screw 100 tightly in each section bends the lower flange 86 to rub against the extension 80 of the other section.

In a similar, alternative embodiment, as best illustrated in FIG. 17, the guide screw 100 also comprises screw threads at the lower end. However, the lower flange hole 92 further comprises a locking screw 110. The locking screw 110 comprises an outer ring 112 disposed on the lower exterior surface of the section, circumscribing the lower flange hole 92, wherein the outer ring 112 is wider than the lower flange hole 92. The locking screw 110 also comprises a hollow tube 114 comprising an exterior surface 116 and an interior surface 118, the hollow tube 114 extending into the lower flange hole 92 from the outer ring 112 such that the exterior surface 116 abuts the lower flange hole 92. Additionally, the interior surface 118 of the hollow tube comprises a helical groove 120 accommodating the screw threads 108 of the guide screw 100. In various embodiments, the locking screw 110 comprises at least one protrusion 122 along the exterior surface 116 of the hollow tube 114 where the hollow tube 114 joins the outer ring 112. This protrusion 122 matches a notch 124 in the lower exterior surface 22, 22' of the lower flange hole 92. The protrusion 122 disposed in the notch 124 prevents rotation of the locking screw 110 in the lower flange hole 92. In these embodiments, screwing the guide screw 100 tightly in the flange holes 90, 92 engages the helical groove 120 in the hollow tube 114 and forces the lower flange 86 toward the upper flange 84 such that the lower flange 86 is compressed against the extension 80 of the other section.

In some of these embodiments, the locking screw 110 comprises two protrusions 122 along exterior surface 116 of the hollow tube 114 where the hollow tube 114 joins the outer ring 112, where each protrusion 122 matches a notch 124 in the lower exterior surface 22, 22' of the lower flange hole 92.

The effectiveness of the mechanisms described immediately above that immobilizes the extension 80 of the two plates relative to each other can be enhanced by roughening at least a portion of the extension 80 and/or the upper flange 84 and/or the lower flange 86 at a point of contact between the extension 80 and upper flange 84 or lower flange 86 to provide friction between the extension 80 and the upper flange 84 and/or lower flange 86. The roughening can be performed by any method, including blasting of the surface with glass beads.

Figure 18A:
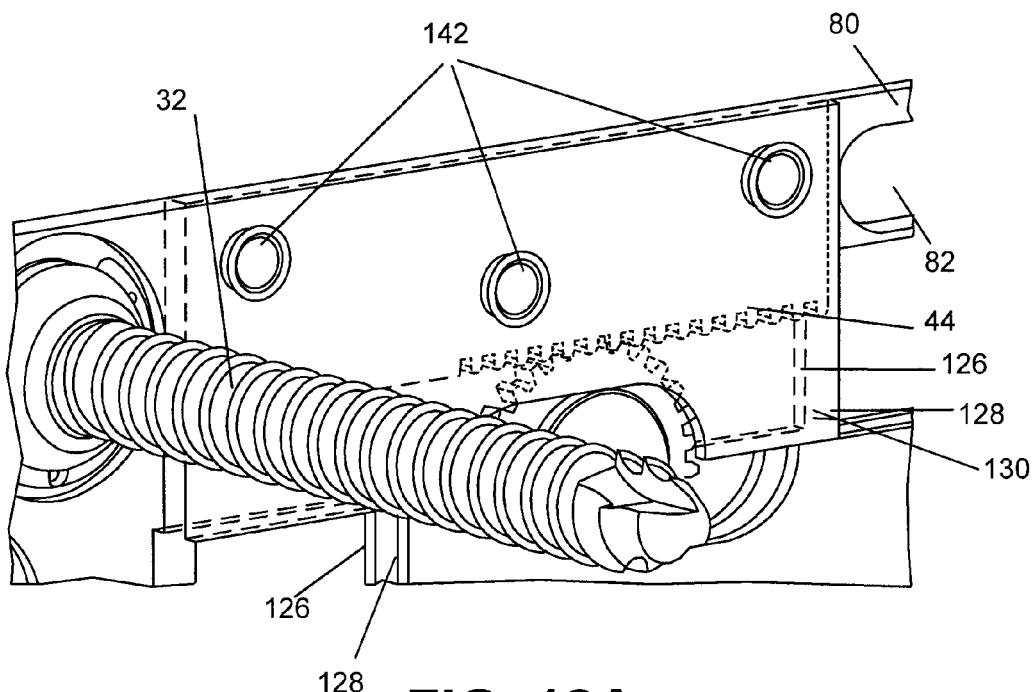
FIG. 18 is a partial cutaway view (A) and a cross-sectional view (B) of a portion of a bone plate in accordance with an illustrative embodiment.
Figures 18B, 18C:
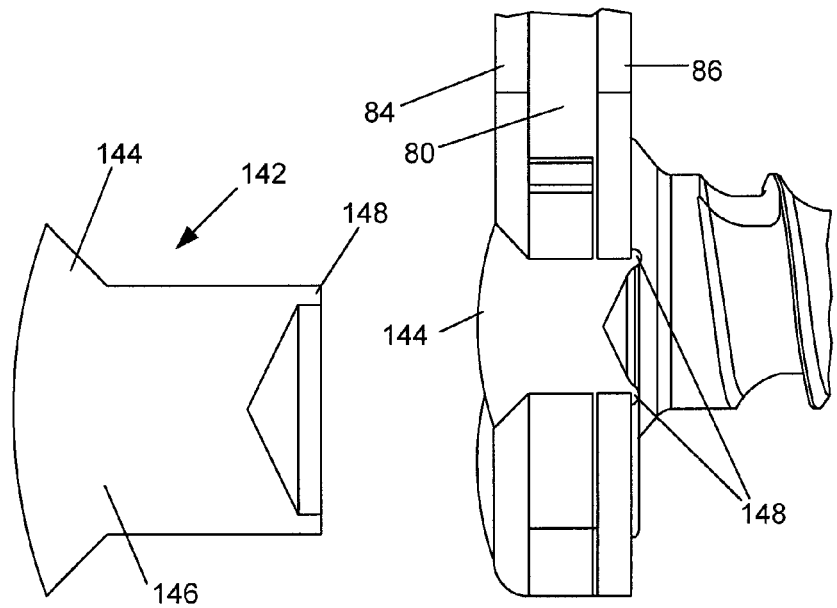
Figure 19A:
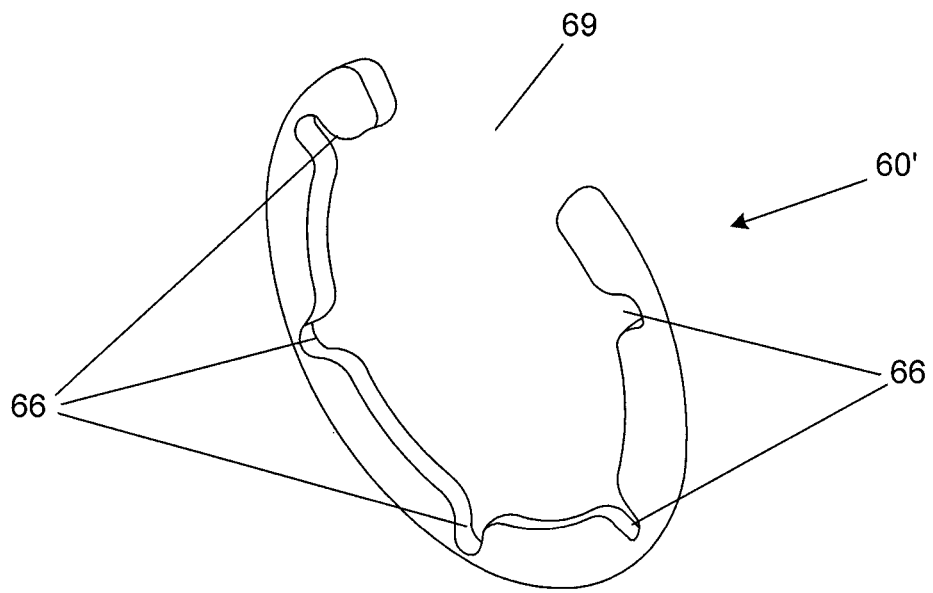
FIG. 19 is perspective views of a locking ring for a bone plate in accordance with an illustrative embodiment.
Figure 19B:
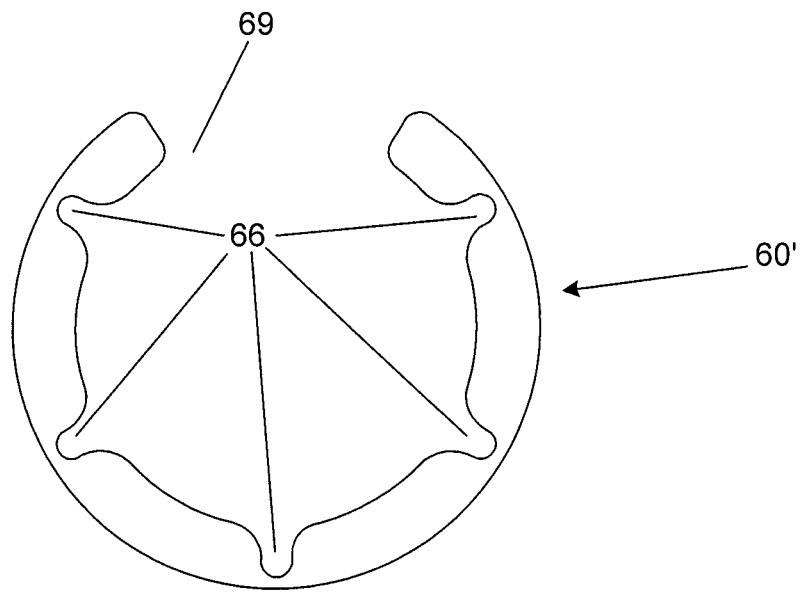

In some embodiments, for example as illustrated in FIGS. 12-16, the extension 80 of each section is continuous with the gear strip 44, 44' of that section. In these embodiments, each section further comprises a wide portion 14 toward the distal end and a narrow portion 16 toward the coupling end, where the wide portion 14 is substantially rectangular and the narrow portion 16 is substantially rectangular, elongate and narrower than the wide portion. The narrow portion 16 comprises an upper half 126 and a lower half 128 forming a space 130 between them that accommodates the gear strip 44, 44'. The narrow portion 16 in these embodiments also comprises at least one rivet hole 140 extending through the upper half 126, the gear strip 44, 44' and the lower half 128. The rivet hole 140 in these embodiments further comprises a rivet 142 extending therethrough. As best illustrated in FIG. 18B, in some embodiments, the rivets comprise a rivet head 144 which prevents the rivet from passing through the rivet hole 140, a rivet body 146 which fits into the rivet hole 140, and a rivet buck-tail 148. The rivet buck-tail is bent outward after the rivet is inserted into the rivet hole 140, preventing the rivet 142 from coming out of the rivet hole 140 and holding the upper half 126, the lower half 128 and gear strip 44 together. The buck-tail 148 can be bent outward with any appropriate tool, for example a pliers or other suitable crimping tool.

The gear strip 44, 44' in these embodiments, continuous with the extension 80, can be of any width. In the embodiments illustrated in FIGS. 12-16, the gear strip 44, 44' extends to the outer edge 24, 24' of the narrow portion 16. Additionally, the narrow portion 16 can comprise any number of rivets. In the embodiments illustrated in FIGS. 12-16, the narrow portion 16 comprises three rivet holes 140 and rivets 142.

Figure 1:
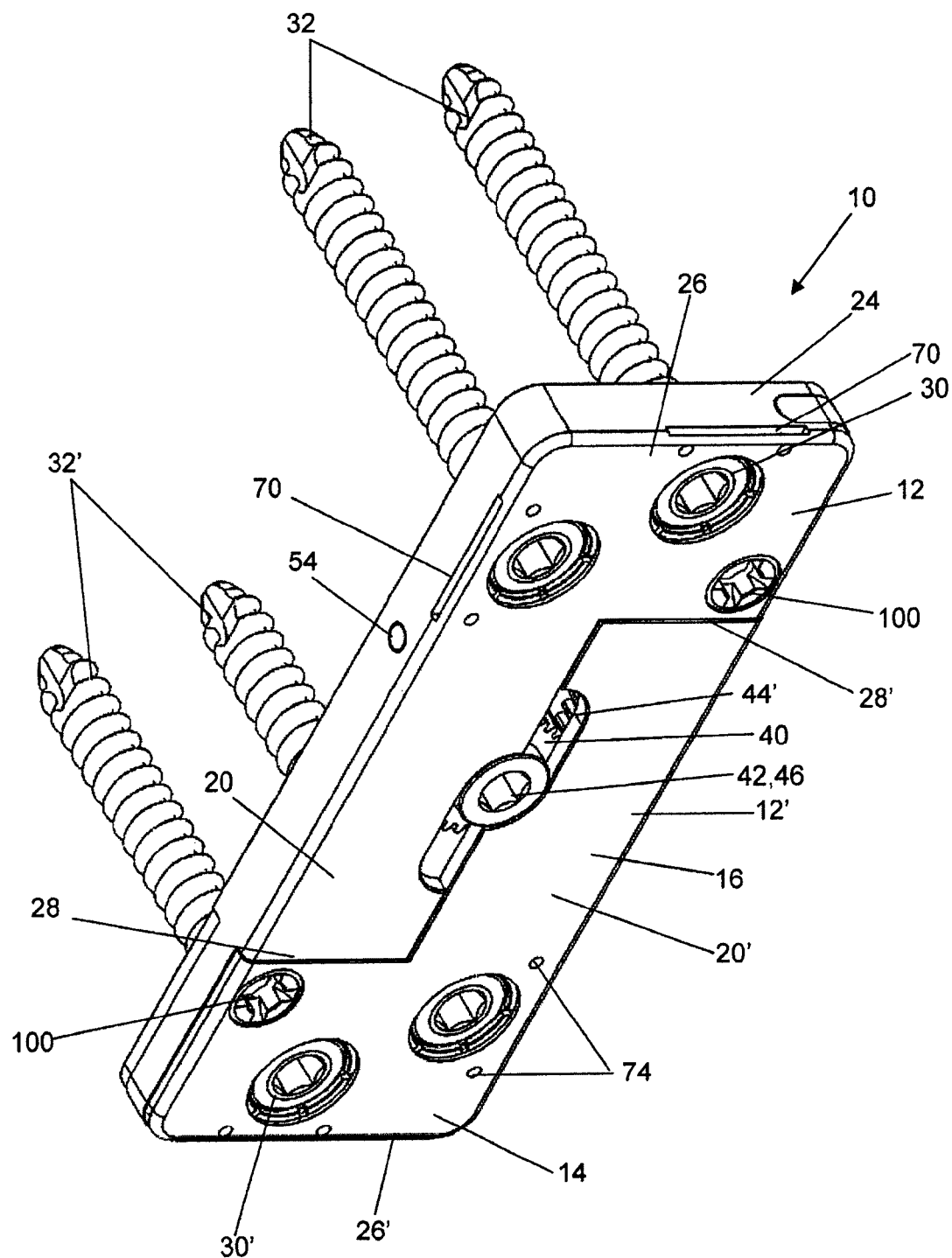
FIG. 1 is a perspective view of the front of a bone plate in the fully closed position in accordance with an illustrative embodiment.
Figure 12A:
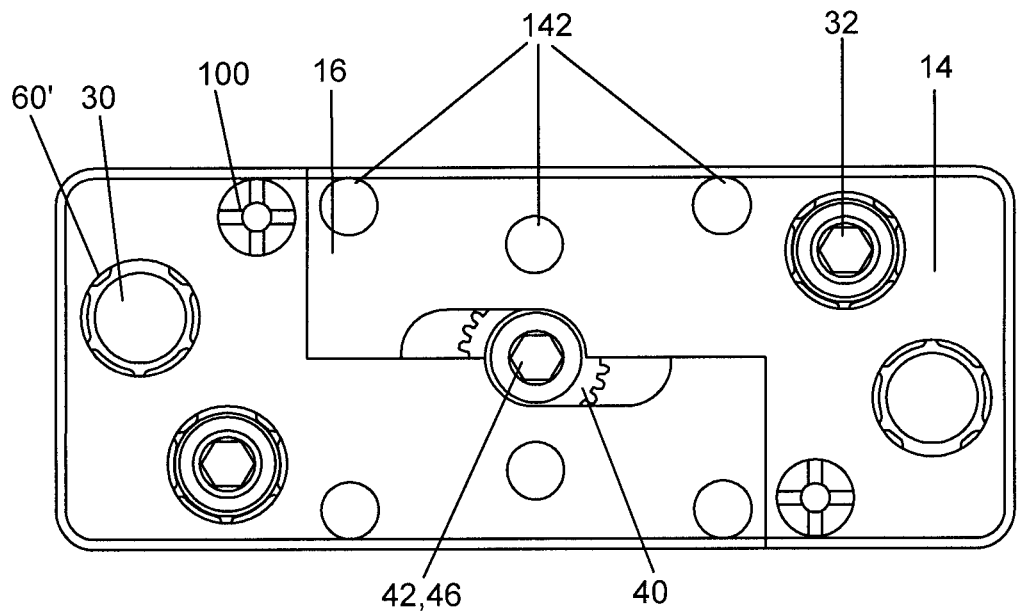
FIG. 12 is a perspective view of the front of a bone plate in the fully closed position (A) and a cutaway view of the front of a bone plate in the fully open position (B) in accordance with an illustrative embodiment.
Figure 12B:
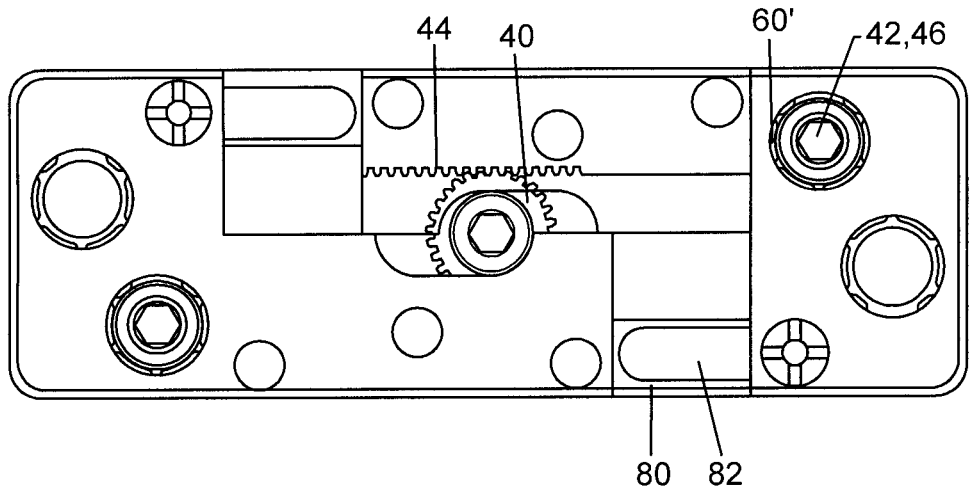
Figure 13:
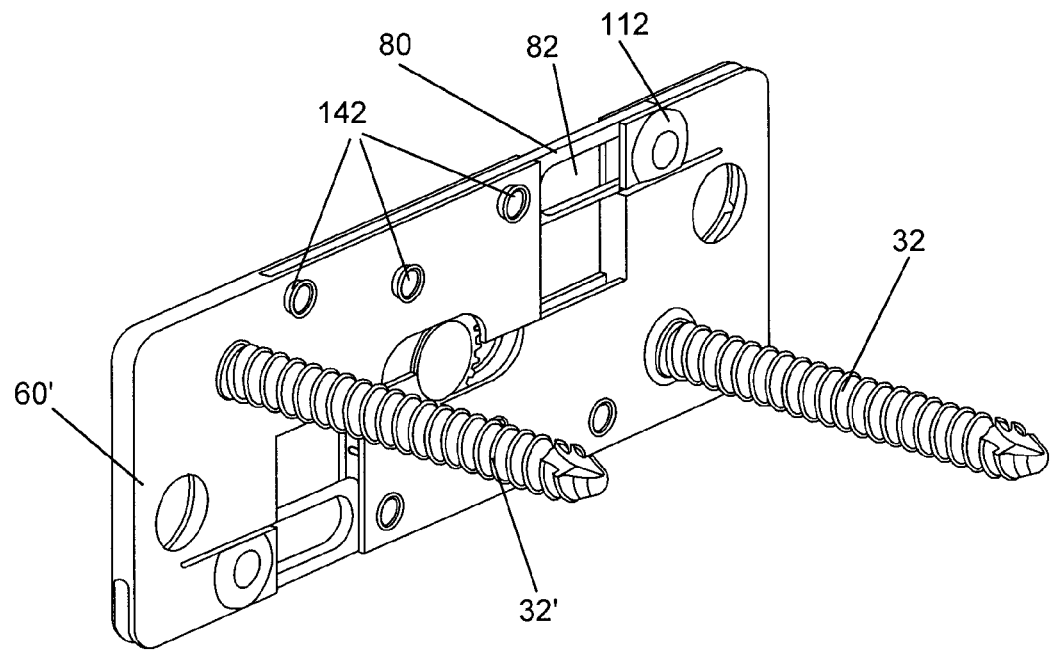
FIG. 13 is a partial cutaway view of the back of a bone plate in the fully open position.
Figure 14A:
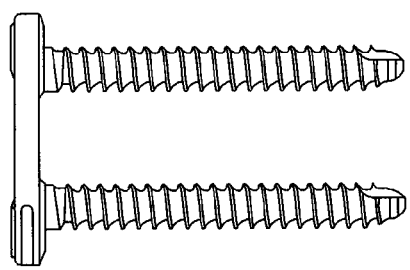
FIG. 14 is a partial cutaway view of the side of one embodiment (A) and another embodiment (B) of bone plates described herein.
Figure 14B:
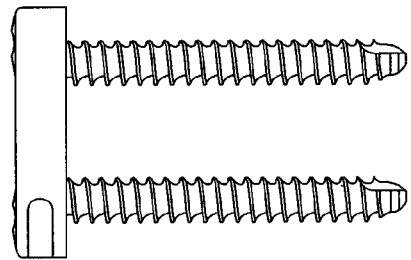
Figure 15:
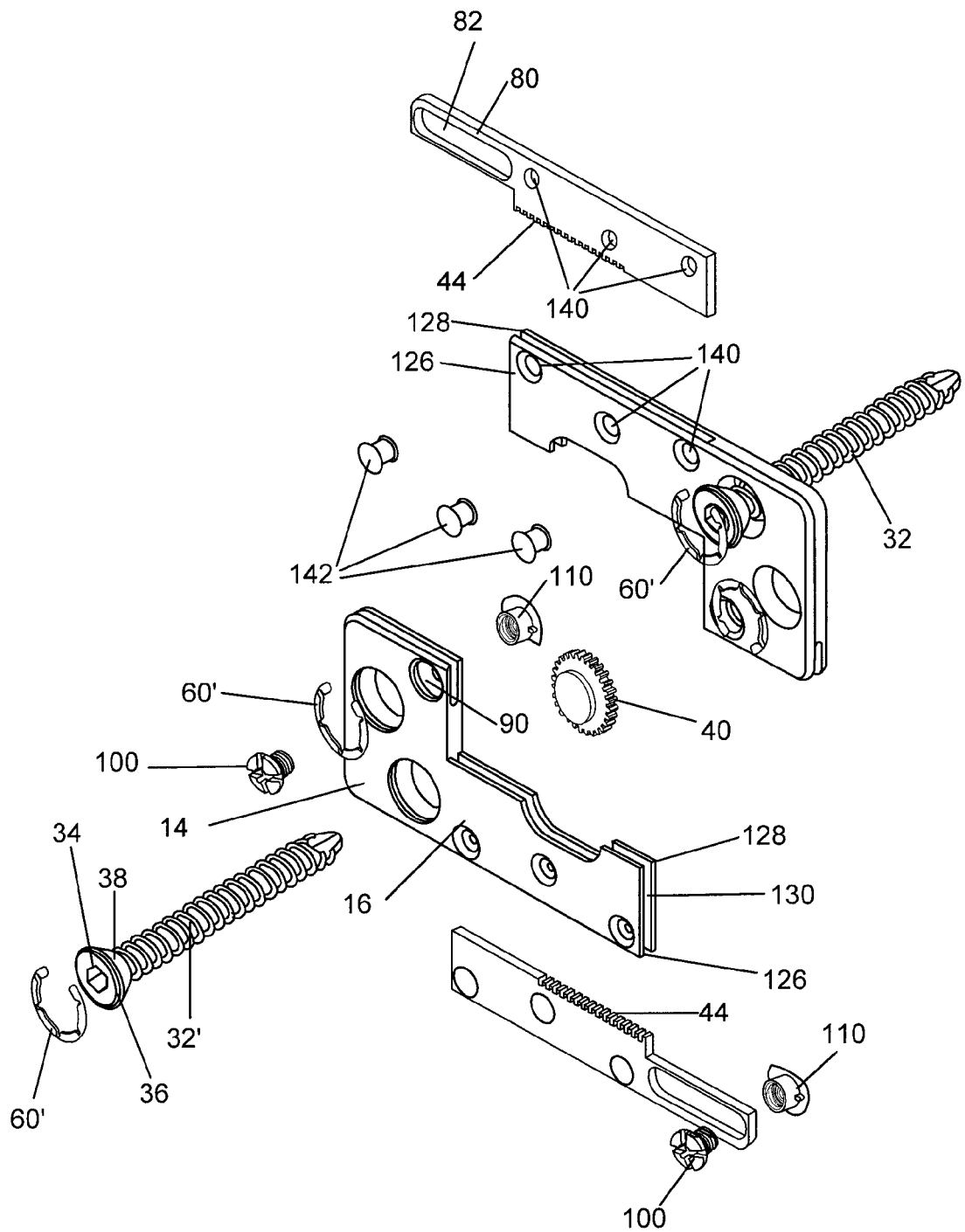
FIG. 15 is an exploded, partial cutaway view of the front of a bone plate in accordance with an illustrative embodiment.
Figure 16:
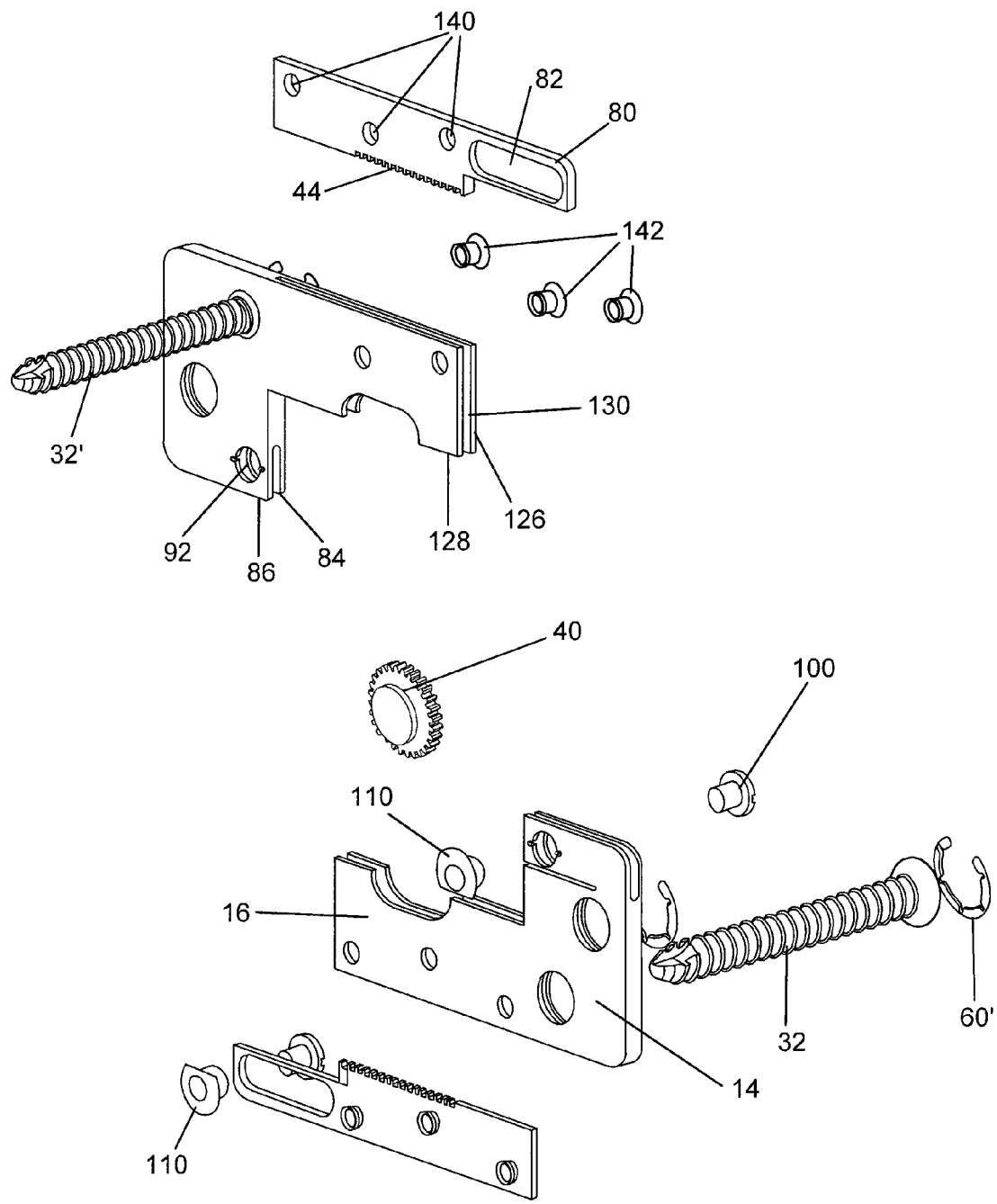
FIG. 16 is an exploded, partial cutaway view of the back of a bone plate in accordance with an illustrative embodiment.
Figure 17A:
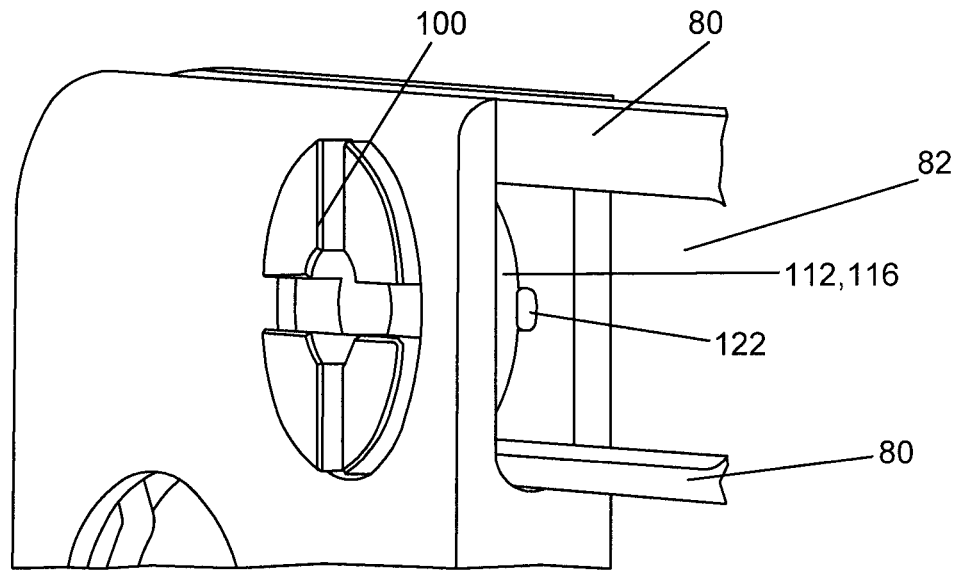
FIG. 17 is a perspective front view (A), an exploded front view (B), an exploded back view (C) and a cross-sectional view (D) of a portion of a bone plate in accordance with an illustrative embodiment.
Figure 17B:
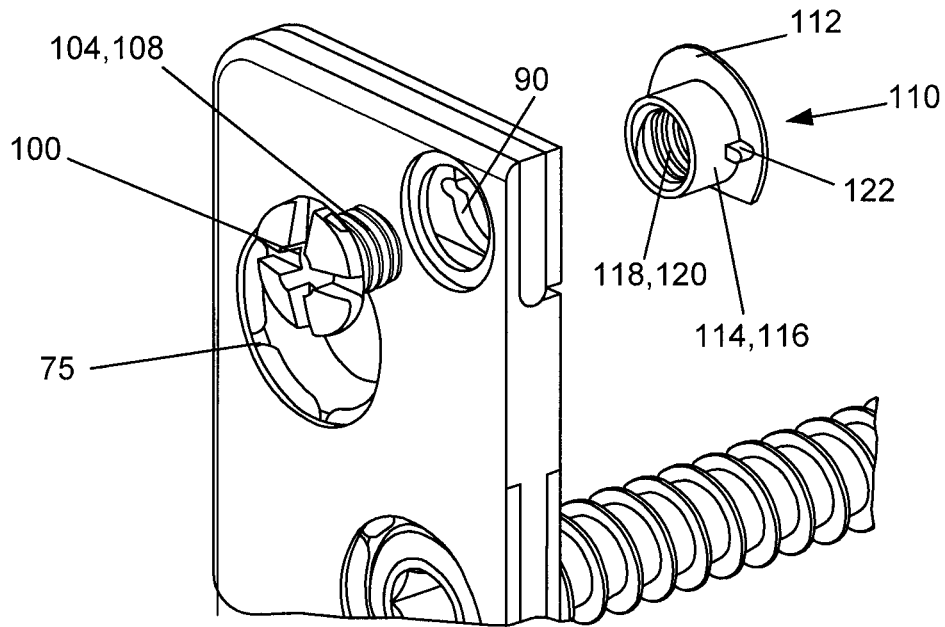
Figure 17C:
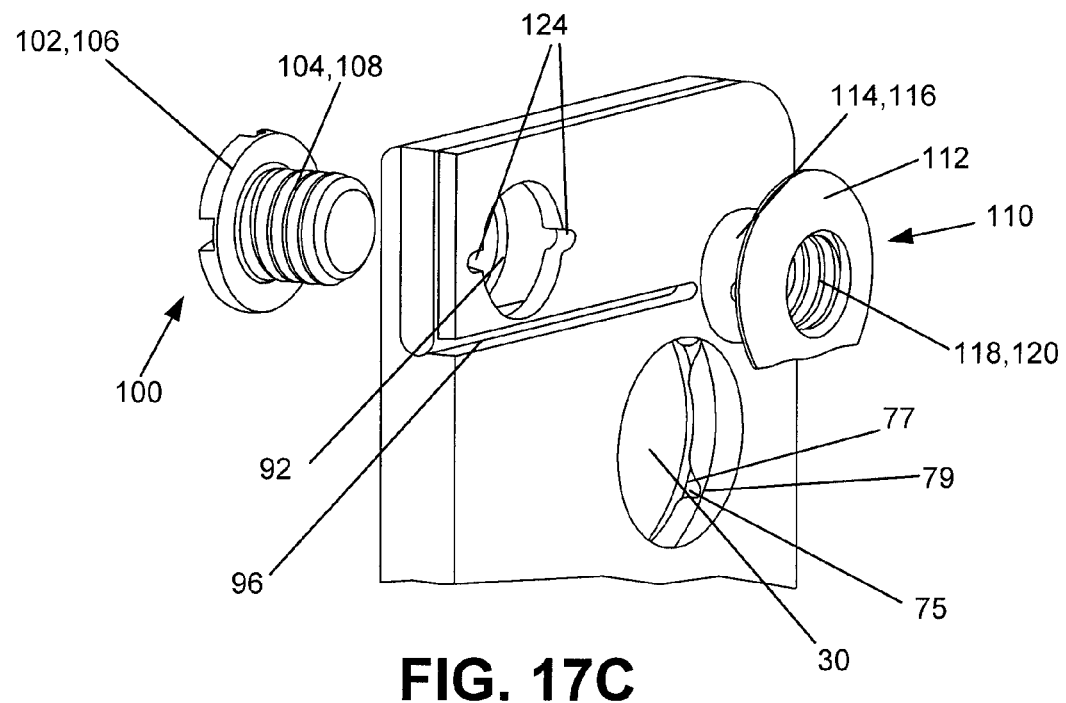
Figure 17D:
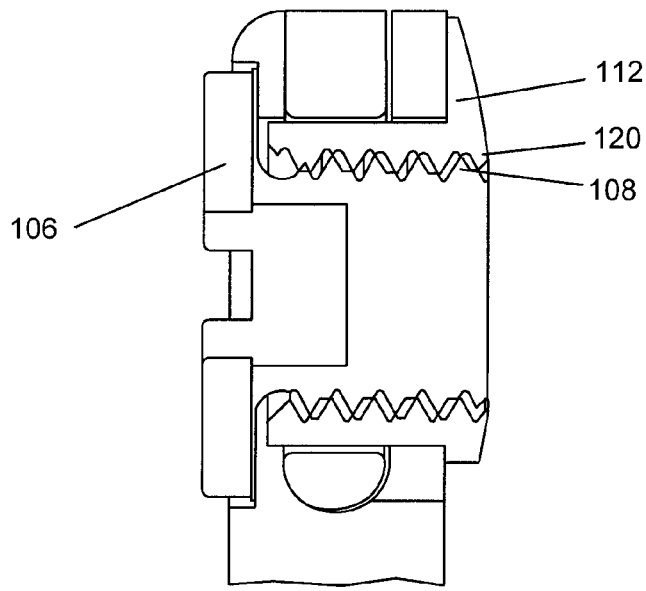

The plates described herein can have any dimensions suitable for attachment to bones. For example, the length of the plate can be about 10 mm, about 25 mm, about 50 mm, about 75 mm, about 100 mm, about 200 mm, about 500 mm, or any length in between. Similarly, the width can be about 5 mm, about 10 mm, about 20 mm, about 50 mm, about 100 mm, about 200 mm, or any width in between. Additionally, the thickness can be about 1 mm, about 2 mm, about 4 mm, about 8 mm, about 20 mm, or any thickness in between. In some embodiments, the plate is about 50 mm in length in the closed position (i.e., the rotating unit fully rotated in the first direction) and about 58.5 mm in length in the fully opened position (i.e., the rotating unit fully rotated in the second direction), and about 20 mm in width. The embodiment illustrated in FIGS. 1-3 is designed to have those dimensions, with a thickness of 4 mm; the embodiment illustrated in FIGS. 12 and 13 is designed to have the length and width described above, with a thickness of 2 mm. FIG. 14 provides an end-on view of these two embodiments, showing those differences in thickness. Although the illustrated embodiments are designed to have the above-described dimensions, plates of the same or similar design are envisioned as having other dimensions.

While the plate in the illustrated embodiments comprises two identical sections, that is not necessary to practice the invention. Further, the applicants contemplate the use of any combination of the above-described features, including, but not limited to, the illustrated embodiment.

The plate can be made of any appropriate material known in the art. Nonlimiting examples of materials that could be used to fabricate the device include (a) titanium, (b) an alloy of titanium with about 6% aluminum and about 4% vanadium, (c) nitinol, (d) stainless steel, and (e) a polymer such as poly ethyl ethyl ketone (PEEK). Additionally, the various components can be made of different materials. For example, the sections can be made of stainless steel while the rivets can be made of a more flexible or softer material, such as rubber or aluminum.

Also provided herein is a method of adjusting the position of a first bone piece with respect to a second bone piece. The method comprises applying any embodiment of the above-described plate to the first bone piece and second bone piece by placing the first section 12 on the first bone piece and the second section 12' on the second bone piece, screwing the bone screw(s) 32 of the first section 12 into the first bone piece and screwing the bone screw(s) 32' of the second section 12' into the second bone piece, and rotating the rotating unit 42 until the first bone piece is in the desired position with respect to the second bone piece. In some embodiments of this method, the rotating unit 42 is a cavity 46 in the gear 40 or a protrusion extending from the gear 40.

The rotating unit can be rotated by hand or by any appropriate tool. In some embodiments, the rotating unit is rotated with a tool that limits the torque applied to the gear to a set amount of force. This allows precise control of applied compression.

In various embodiments, the rotating unit is a motor. Particularly useful embodiments here is where the motor compresses the first bone piece against the second bone piece to a set amount of force, for example where the motor maintains a set force over time, or varies the set amount of force over time.

Another method of adjusting the position of a first bone piece with respect to a second bone piece is additionally provided. The method comprises applying the plate of either of the illustrated embodiments to the first bone piece and second bone piece by placing the first section 12 on the first bone piece and the second section 12' on the second bone piece, screwing the bone screws 32 of the first section 12 and second section 12' into the first bone piece until the head 34 of each bone screw 32 passes its locking ring 60 or 60', rotating the hexagonal cavity 46 in the gear 40 until the first bone piece is in the desired position with respect to the second bone piece, and screwing the guide screw 100 in the flanges 84, 86 of each section until the lower flanges 86 are forced against the extension 80 of the other section.

In some embodiments, the hexagonal cavity 46 is rotated to compress the first bone piece against the second bone piece to a set amount of force. Such a rotation of the hexagonal cavity 46 can be executed using a tool that measures or limits the torque applied to the gear to the set amount of force. Such tools are known in the art.

Any of the above-described methods can be used with any two bone pieces where compression of the two bone pieces is desired. For example, the bone pieces may be two bones to be fused. Any two bone pieces can be fused using the plate described herein, including where the two bones are adjacent vertebrae, where the bone pieces are two pieces of a surgically cut bone, or where the bone pieces are two pieces of a fractured bone. Such a fracture can be a complete fracture or an incomplete fracture, in a long bone, a short bone, a flat bone, an irregular bone (e.g., a vertebra), or a sesamoid bone. It is contemplated that the two bone pieces can be connected, e.g., by periosteum, for example in an incomplete fracture.

Additionally, any of the above-described methods can be used with any two bone pieces where distraction of the two bone pieces is desired. In some embodiments of these methods, the rotating unit is a motor, e.g., a micro motor as described above. In various of these embodiments, for example when practicing distraction osteogenesis, the motor continues to rotate the gear 40 to distract the bone pieces for more than one day after the plate is applied, to allow new bone to grow between the bone pieces. Here, the bone pieces are two pieces of a long bone that has been surgically cut. The motor can rotate the gear to distract the bone pieces at any rate of distraction, for example about 1 mm per day.

The locking rings described above are useful for preventing a bone screw from backing out of any bone plate. Thus, a locking ring 60 suitable for preventing a bone screw 32 having a head 34 and spiraling threads from backing out of a bone plate is provided. The locking ring 60 comprises an interior edge 62 and an exterior edge 64; a plurality of radial slots 66 partially cut through the locking ring from the interior edge 62 toward the exterior edge 64; and a means for allowing expansion of the locking ring diameter. In these embodiments, the locking ring 60 is narrower than the head 34 of the bone screw 32 and wider than the threads of the bone screw 32. The locking ring 60 can comprise any means for allowing expansion of the locking ring diameter. Examples include making at least a part of the locking ring from an elastic material or an elastic type material. In the embodiment illustrated in FIG. 7B, the means for allowing expansion of the locking ring is a radial cut 68 through the ring 60 from the interior edge 62 through the exterior edge 64. In other embodiments, the means for allowing expansion of the locking ring diameter is a radial cut partially through the locking ring and at least a portion of the locking ring comprising an elastic material or an elastic type material.

An alternative locking ring 60', suitable for preventing a bone screw 32 having a head 34 and spiraling threads from backing out of a bone plate, is also provided. This locking ring 60' comprises an interior edge 62 and an exterior edge 64; a plurality of radial slots 66 partially cut through the locking ring 60' from the interior edge 62 toward the exterior edge 64; a means for allowing expansion of the locking ring diameter, and a means for allowing contraction of the locking ring diameter. As with the previously described locking ring 60, this locking ring 60' is narrower than the head 34 of the bone screw 32 and wider than the threads of the bone screw 32.

This locking ring 60' can also comprise any means for allowing expansion and contraction of the locking ring diameter. Examples include making at least a part of the locking ring from an elastic material or an elastic type material. In the embodiment illustrated in FIG. 19, the means for allowing expansion of the locking ring is a radial section of the locking ring removed 69.

Any of the locking rings described above can be constructed to accommodate any bone screw, for example a bone screw having any diameter from 1-10 mm. In some embodiments, the bone screw has a diameter of about 3.5 mm.

Also provided is a method of preventing a bone screw from backing out of a bone plate using any of the above-described locking rings. In these methods, the bone plate comprises the bone screw, a screw hole an outer edge and a ring slot. The ring slot in these embodiments circumscribes the bone screw hole and extends to the outer edge of the plate. Additionally, the ring slot comprises a ring slot upper surface and a ring slot lower surface, the bone screw hole passing through the ring slot upper surface and the ring slot lower surface. The bone screw in these embodiments has a head wider than the interior edge of the locking ring, a spiraling thread, and a flat outer face and tapered inner face, and the bone screw hole has a diameter wider than the screw head at the upper surface of the plate and the ring slot upper surface but narrower than the locking ring, and a diameter narrower than the screw head at the ring slot lower surface. The method of these embodiments comprises placing the locking ring through the ring slot to the bone screw hole, placing the bone screw hole over a bone, putting the bone screw into the bone screw hole, and screwing the bone screw into the bone such that the tapered inner face of the head of the screw encounters the locking ring and expands the locking ring radially outward until the head of the bone screw passes the interior edge of the locking ring, allowing the locking ring to resume its original shape, extending over the flat outer face of the bone screw.

In these methods, the locking ring is prevented from exiting the outer edge of the ring slot by any method known in the art. In some embodiments, the locking ring is prevented from exiting the outer edge of the ring slot by at least one slot pin disposed through a slot pin hole extending from the upper exterior of the section adjacent to the bone screw hole.

Additionally provided herein is a method of preventing a bone screw from backing out of a bone plate using the locking ring described above that comprises a means for allowing both expansion and contraction of the locking ring diameter. In these methods, the bone plate comprises the bone screw, a screw hole an outer edge and a ring seat. The ring seat is disposed below the upper exterior surface of the plate circumscribing the bone screw hole. As such, the ring seat allows placement of a locking ring by contracting the diameter of the locking ring and placing the locking ring into the ring seat. Additionally, the ring seat comprises a ring seat upper surface and a ring seat lower surface, the bone screw hole passing through the ring seat upper surface and the ring seat lower surface. Further, the bone screw hole has a diameter wider than the screw head, but narrower than the locking ring, at the upper surface of the plate and the first ring seat upper surface, and a diameter narrower than the screw head at the ring seat lower surface. The method of these embodiments comprises contracting the diameter of the locking ring and placing the locking ring into the ring seat, placing the bone screw hole over a bone, putting the bone screw into the bone screw hole, and screwing the bone screw into the bone such that the tapered inner face of the head of the screw encounters the locking ring and expands the locking ring radially outward until the head of the bone screw passes the interior edge of the locking ring, allowing the locking ring to resume its original shape, extending over the flat outer face of the bone screw.

Figure 20:
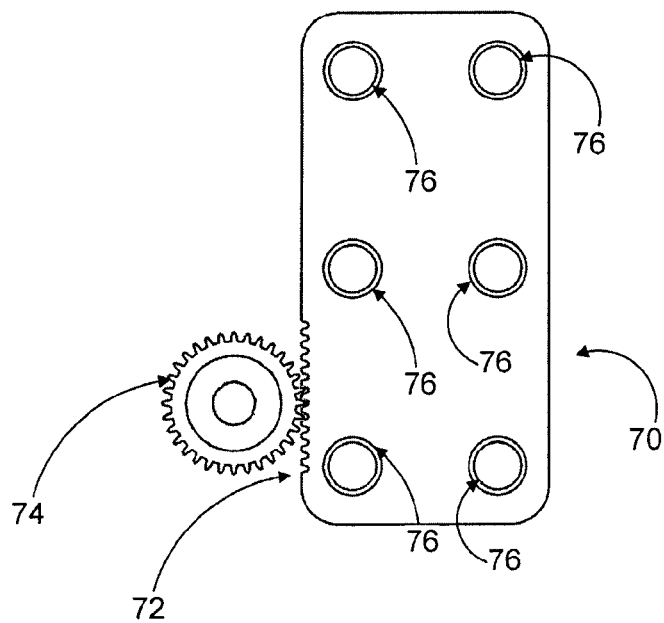
FIG. 20 depicts one embodiment including a plate having a rack located on one side of the plate.

FIG. 20 depicts one embodiment including a plate 70 having a rack 72 located on one side of the plate 70. The plate 70 includes a plurality of screw hole openings 76 which are configured to hold a bone screw using any of the above mentioned methods. Consistent with this embodiment, an external gear 74 engages the rack 72 causing the plate 70 to move along an axis parallel to the rack 72. Because the gear 74 is external to the plate 70, the plate 70 can be made thinner than the previous embodiments. In one embodiment, the gear 74 is a bevel gear.

Figure 21:
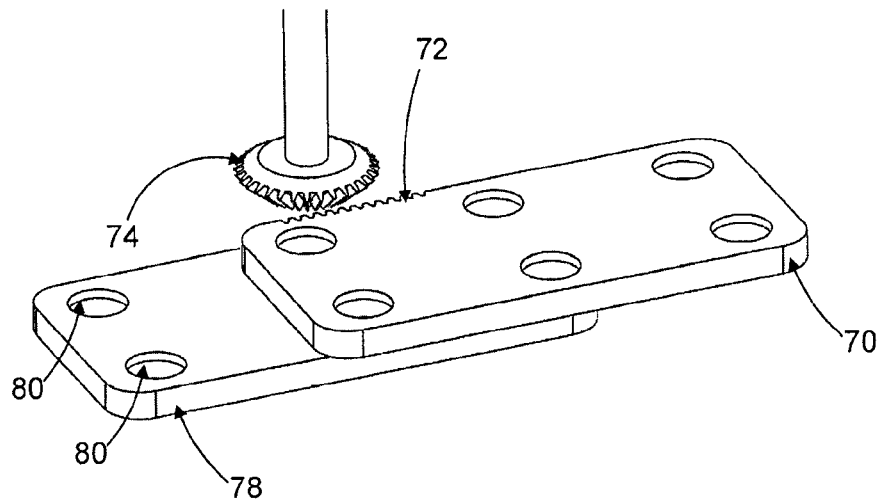
FIG. 21 depicts one embodiment with a top plate having a rack positioned on top of a lower plate that includes a plurality of screw holes.

FIG. 21 depicts one embodiment with a top plate 70 having a rack 72 positioned on top of a lower plate 78 that includes a plurality of screw holes 80. As the figure depicts, a bevel gear 74 engages the rack 72 causing the upper plate 70 to move relative to the lower plate 78. As the bevel gear 74 rotates clockwise (when viewed from the upper side, i.e., the side of the upper plate 70), the upper plate 70 is moved towards the lower plate 78. Conversely, when the bevel gear 74 is rotated counterclockwise, the upper plate 70 moves away from the lower plate 78. In one embodiment, the rack 72 is located on the lower plate 76 only. In another embodiment, the rack 72 is located on both the upper plate 70 and the lower plate 78. Consistent with this embodiment, the bevel gear 74 simultaneously engages the rack 72 on both the upper plate 70 and the lower plate 78. In another embodiment, a rack 72 is located on the upper plate 70 and the lower plate 78 on opposing sides. In yet another embodiment, a rack 72 is located on the upper plate 70 and the lower plate 78 on different sides and each positioned adjacent to opposing ends of each plate.

As FIG. 21 depicts, the lower plate 78 is attached to a bone segment using any of the previously disclosed methods and the upper plate 70 is attached to the same bone segment. When the bevel gear 74 engages the rack 72, the upper plate 70 is pulled towards the lower plate 78, thereby compressing the bone segment together. The upper plate 70 and lower plate 78 are secured to the bone segment using any of the previously described methods.

Figure 22:
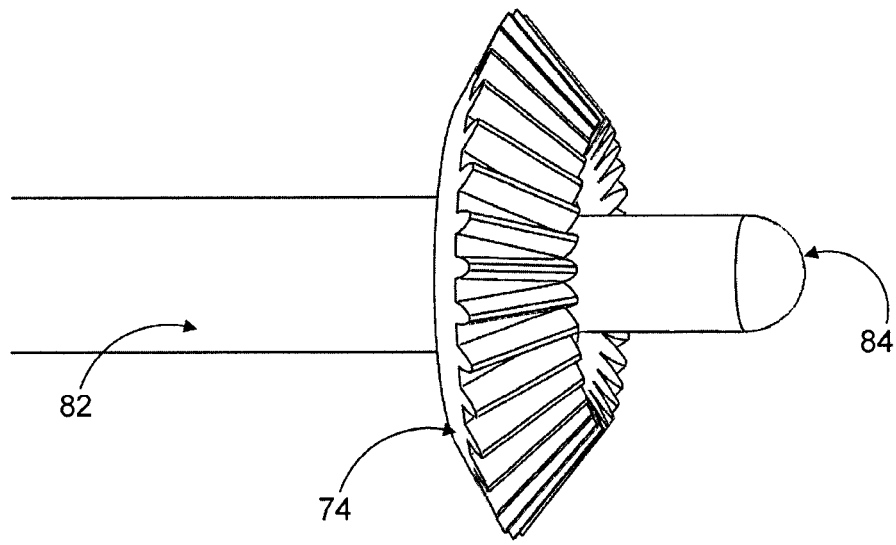
FIG. 22 depicts one embodiment of the bevel gear.

FIG. 22 depicts one embodiment of the bevel gear 74. As the figure depicts, the bevel gear 74 is coupled to a rotational shaft 82 and a side of the bevel gear 74 closest to the end of the shaft 84 is smaller in diameter than the side of the gear located farther from the end of the shaft 84. In one embodiment, the end of the shaft 84 is used as a pilot nose or projection in conjunction with a hole, indentation, mating surface or corresponding guide on the lower plate 78 (not shown) which controls and/or helps maintain stability of the axis of the shaft 82 in relation to the upper plate 70 and/or lower plate 78 and also assists in providing torque to the bevel gear 74 and the rack 72.

Figure 23:
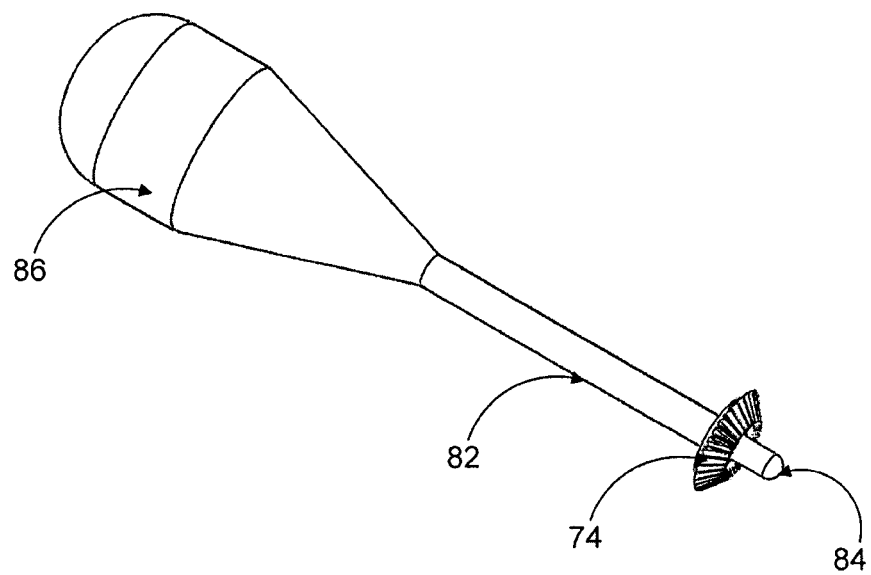
FIG. 23 depicts a motor coupled to the shaft of the bevel gear.

FIG. 23 depicts a motor 86 coupled to the shaft 82 of the bevel gear 74. Similar to the previous embodiments, the bevel gear 74 engages the rack 72 which causes the upper plate 70 and lower plate 78 to move towards each other to compress two bone segments attached to the upper plate 70 and lower plate 78. As one having ordinary skill in the art would appreciate, since the rack 72 is located on the side of the plate 70 opposed to the configuration of the previous embodiments, the plate 70 is thinner than the previous embodiments. Additionally, the bevel gear 74 only engages with the rack 72 to compress the upper plate 70 and the lower plate 78 together. Accordingly, the bevel gear 74 is not present when the two plates are not being moved. In another embodiment, the motor 86 is a handle which is manually torqued.

Figure 24:
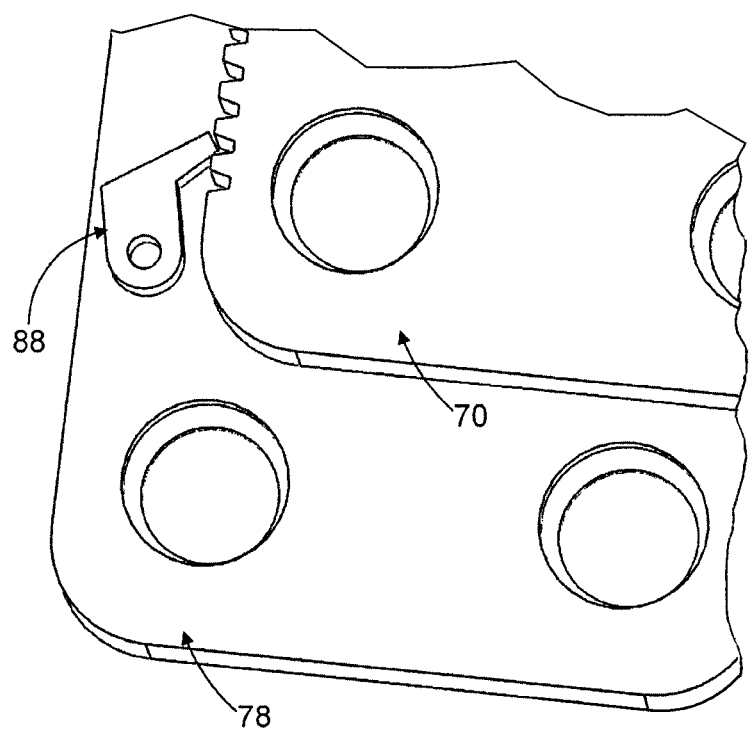
FIG. 24 depicts one embodiment of an upper plate positioned over a lower plate.

FIG. 24 depicts one embodiment of an upper plate 70 positioned over a lower plate 78. As the figure depicts, the side of the upper plate 70 having the rack 72 is offset from the corresponding side of the lower plate 78 by a distance d. In one embodiment, the distance d is sufficient to accommodate the end of the shaft 84 such that the end of the shaft acts as a pilot nose used to control the axis of the shaft 84 relative to the lower plate 78. In another embodiment. The lower plate 78 includes a locking unit 88 having one end rotatively coupled to the lower plate 78 and one end of the locking unit 88 engaging the teeth of the rack 72 preventing the upper plate 70 from moving in relation to the lower plate 78. In another embodiment, the locking unit 88 is a pawl.

Other embodiments within the scope of the claims herein will be apparent to one skilled in the art from consideration of the specification or practice of the invention as disclosed herein. It is intended that the specification be considered exemplary only, with the scope and spirit of the invention being indicated by the claims.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

The invention claimed is:

1. A plate for adjusting a position of a first piece of bone with respect to a second piece of bone, the plate comprising:
    a first section comprising a first upper exterior surface, a first lower exterior surface, a first outer edge, a first distal end, a first coupling end across the first section from the first distal end, at least one first section bone screw hole, and a first bone screw countersunk in one of the at least one first section bone screw hole, the one of the at least one first section bone screw hole including a first locking ring that prevents the first bone screw from backing out of the respective one of the at least one first section bone screw hole;
    a second section comprising a second upper exterior surface, a second lower exterior surface, a second outer edge, a second distal end, a second coupling end across the second section from the second distal end, at least one second section bone screw hole, and a second bone screw countersunk in one of the at least one second section bone screw hole, the one of the at least one second section bone screw hole including a second locking ring that prevents the second bone screw from backing out of the respective one of the at least one second section bone screw hole;
    a first ring slot circumscribing the one of the at least one first section bone screw hole disposed between the first upper exterior surface and the first lower exterior surface of the first section and extending to the first outer edge;
    a second ring slot circumscribing the one of the at least one second section bone screw hole disposed between the second upper exterior surface and the second lower exterior surface of the second section and extending to the second outer edge;
    a gear disposed between the first section and the second section, the gear comprising a rotating unit;
    a first section gear strip engaging the gear and coupled to the first section; and
    a second section gear strip engaging the gear and coupled to the second section,
    wherein rotating the rotating unit in a first direction rotates the gear on the first section gear strip and the second section gear strip, to move the first section toward the second section, and rotating the rotating unit in a second direction rotates the gear on the first section gear strip and the second section gear strip to move the first section away from the second section,
    wherein each of the first and second locking rings comprises an interior edge and an exterior edge, a plurality of radial slots partially cut through each of the first and second locking rings from the interior edge toward the exterior edge, and an expansion unit which allows expansion of a diameter of each of the first and second locking rings,
    wherein each of the first and second bone screws comprises a head wider than an interior dimension defined by the interior edge of the respective first or second locking ring and having a flat outer face and a tapered inner face, and
    wherein each of the first locking ring and the second locking ring is disposed in a respective one of the first and second ring slots and is prevented from exiting the respective first or second ring slot at the respective first outer edge or second outer edge by at least one slot pin, each of the at least one slot pin disposed through a slot pin hole extending from the respective first or second upper exterior surface of the respective first or second section adjacent to the respective one of the at least one first section bone screw hole or the respective one of the at least one second section bone screw hole.

2. The plate of claim 1, wherein each of the first section and the second section comprises a wide portion toward the respective first distal end or second distal end and a narrow portion toward the respective first coupling end or second coupling end, wherein each wide portion is substantially rectangular and each narrow portion is substantially rectangular, elongate and narrower than the respective wide portion.

3. The plate of claim 2, wherein each of the one of the at least one first section bone screw hole and the one of the at least one second section bone screw hole is disposed in the wide portion of the respective first or second section.

4. The plate of claim 1, wherein the second direction is opposite the first direction.

5. The plate of claim 1, wherein the rotating unit is a cavity in the gear or a protrusion extending from the gear.

6. The plate of claim 1, wherein the rotating unit is a motor.

7. The plate of claim 6, wherein the motor is radio controlled.

8. The plate of claim 1, wherein the first section gear strip is integral with the first section and the second section gear strip is integral with the second section.

9. The plate of claim 1, wherein the first section gear strip is coupled to the first section by a first gear strip coupling unit, and the second section gear strip is coupled to the second section by a second gear strip coupling unit.

10. The plate of claim 1, wherein the first and second pieces of bone are two pieces of one selected from the group of a surgically cut bone, a fractured bone, a complete fracture, an incomplete fracture, a fracture in a long bone, a fracture in a short bone, a fracture in a flat bone, a fracture in an irregular bone, a fracture in an irregular bone in a vertebra, or a fracture in a sesamoid bone.

11. The plate of claim 1, wherein the expansion unit of each locking ring is a radial cut that extends entirely through the locking ring.

12. The plate of claim 1, wherein at least a portion of each locking ring is comprised of an elastic material or an elastic type of material.

\* \* \* \* \*